(12) United States Patent
Srivastava et al.

(10) Patent No.: US 7,531,318 B2
(45) Date of Patent: May 12, 2009

(54) SCREENING OF AGENTS FOR ACTIVITY AGAINST ISCHEMIC MYOCARDIAL INSULTS

(75) Inventors: Deepak Srivastava, Orinda, CA (US); Ildiko Bock-Marquette, Dallas, TX (US); Ankur Saxena, Sugar Land, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 228 days.

(21) Appl. No.: 11/209,199

(22) Filed: Aug. 22, 2005

(65) Prior Publication Data

US 2006/0121496 A1 Jun. 8, 2006

Related U.S. Application Data

(60) Provisional application No. 60/630,602, filed on Nov. 24, 2004, provisional application No. 60/602,884, filed on Aug. 20, 2004.

(51) Int. Cl.
*C12Q 1/02* (2006.01)
(52) U.S. Cl. ............................. 435/29; 435/15; 435/183
(58) Field of Classification Search ........................ None
See application file for complete search history.

(56) References Cited

U.S. PATENT DOCUMENTS

| 4,297,276 | A | 10/1981 | Goldstein et al. | ........... 530/324 |
|---|---|---|---|---|
| 4,395,404 | A | 7/1983 | Low et al. | ..................... 514/14 |
| 4,543,340 | A | 9/1985 | Goldstein et al. | ........... 436/542 |
| 5,578,570 | A | 11/1996 | Goldstein et al. | ............. 514/12 |
| 5,593,964 | A | 1/1997 | Goldstein et al. | ............. 514/12 |
| 2003/0060405 | A1 | 3/2003 | Kleinman et al. | ............. 514/12 |
| 2003/0144204 | A1 | 7/2003 | Spencer | ....................... 514/12 |
| 2004/0067227 | A1 | 4/2004 | Goldstein | ............... 424/130.1 |
| 2004/0122077 | A1 | 6/2004 | Walsh | ......................... 514/423 |
| 2004/0131626 | A1 | 7/2004 | Goldstein | ............... 424/184.1 |

FOREIGN PATENT DOCUMENTS

| WO | WO 97/23625 | 7/1997 |
|---|---|---|
| WO | WO 99/57305 | 11/1999 |
| WO | WO 00/06190 | 2/2000 |
| WO | WO 00/20025 | 4/2000 |
| WO | WO 00/62605 | 10/2000 |
| WO | WO 00/77190 | 12/2000 |
| WO | WO 03/020215 | 3/2003 |

OTHER PUBLICATIONS

Fujio et al, "Akt Promotes Survival of Cardiomyocytes In Vitro and Protects Against Ischemia-Reperfusion Injury in Mouse Heart,"(Circulation), 2000, vol. 101, pp. 660-667.*
Persad et al, "Inhibition of integrin-linked kinase (ILK) suppresses activation of protein kinase B/Akt and induces cell cycle arrest and apoptosis of PTEN-mutant prostate cancer cells," (PNAS), Mar. 28, 2000, vol. 97, No. 7, pp. 3207-3212.*
Lu et al., "Integrin linked kinase overexpression suppresses pro-inflammatory signaling in heart," *Circulation*, 108:IV-77, 2003.
Schauer et al., "Visualizing Gene Expression with Luciferase Fusions," *Trends in Biotechnology*, 6:23-27, 1988.
Bock-Marquette et al., "Thymosin β4 activates integrin-linked kinase and promotes cardiac cell migration, survival and cardiac repair", *Nature*, 432:466-472, 2004.
Brazil et al., "PKB binding proteins. Getting in on the Akt," *Cell*, 111:293-303, 2002.
Delcommenne et al., "Phosphoinositide-3-OH kinase-dependent regulation of glycogen synthase kinase 3 and protein kinase B/AKT by the integrin-linked kinase," *Proc. Natl Acad. Sci. USA*, 95:11211-11216, 1998.
Depre et al., "Program of cell survival underlying human and experimental hibernating myocardium," *Circ Res.*, 95(4):433-40, 2004.
Frohm et al., "Biochemical and antibacterial analysis of human wound and blister fluid,"*Eur. J. Biochem.*, 237:86-92, 1996.
Fukuda et al., "PINCH-1 ia an obligate partner of integrin-linked kinase (ILK) functioning in cell shape modulation, motility, and survival," *J. Biol. Chem.*, 278:51324-51333, 2003.
Gomez-Marquez et al., "High levels of mouse thymosin beta4 mRNA in differentiating P19 embryonic cells and during development of cardiovascular tissues," *Biochim. Biophys. Acta*, 1306:187-193, 1996.
Grant et al., "Thymosin beta4 enhances endothelial cell differentiation and angiogenesis," *Angiogenesis*, 3:125-135, 1999.
Hannigan et al., "Regulation of cell adhesion and anchorage-dependent growth by a new $β_1$-integrin-linked protein kinase," *Nature*, 379:91-96, 1996.
Hertzog et al., "The beta-thymosin/WH2 domain; structural basis for the switch from inhibition to promotion of actin assembly," *Cell*, 117:611-623, 2004.
Huang and Wang, "Bone marrow endothelial cells secrete thymosin beta4 and AcSDKP," *Exp. Hematol.*, 29:12-18, 2001.
Huff et al., "beta-Thymosins, small acidic peptides with multiple functions," *Int. J. Biochem. Cell Biol.*, 33:205-220, 2001.
Li et al., "Integrin-linked kinase is localized to cell-matrix focal adhesions but not cell-cell adhesion sites and the focal adhesion localization of integrin-linked kinase is regulated by the PINCH-binding ANK repeats," *J. Cell Sci.*, 112:4589-4599, 1999.
Lin and and Morrison-Bogorad, "Developmental expression of mRNAs encoding thymosins beta 4 and beta 10 in rat brain and other tissues," *J. Mol. Neurosci.*, 2:35-44, 1990.
Malinda et al., "Thymosin beta4 accelerates wound healing," *J. Invest. Dermatol.*, 113:364-368, 1999.
Mangi et al., "Mesenchymal stem cells modified with Akt prevent remodeling and restore performance of infarcted hearts," *Nature Med.*, 9:1195-1201, 2003.
Marinissen et al., "The small GTP-binding protein RhoA regulates c-jun by a ROCK-JNK signaling axis," *Mol. Cell*, 14:29-41, 2004.

(Continued)

*Primary Examiner*—Cecilia Tsang
*Assistant Examiner*—Amanda P Wood
(74) *Attorney, Agent, or Firm*—Fulbright & Jaworski, LLP

(57) ABSTRACT

Integrin-linked kinase (ILK) and Akt/protein kinase B (PKB) are important mediators of signaling in cardiomyocytes and can both prevent damage and promote healing associated with ischemic injury to the heart. Thus, the present invention provides for methods of screening for agents that increase the expression of ILK and/or Akt/PKB. Methods of treatment based on such agents are also provided.

16 Claims, 5 Drawing Sheets
(5 of 5 Drawing Sheet(s) Filed in Color)

OTHER PUBLICATIONS

Nikolopoulos and Turner, "Actopaxin, a new focal adhesion protein that binds paxillin LD motifs and actin and regulates cell adhesion," *J. Cell Biol.*, 151:1435-1448, 2000.

Olave et al., "Nuclear actin and actin-related proteins in chromatin remodeling," *Annu. Rev. Biochem.*, 71:755-781, 2002.

Olski et al., "Parvin, a 42 kDa focal adhesion protein, related to the alpha-actinin superfamily," *J. Cell Sci.*, 114:525-538, 2001.

Philip et al., "Thymosin beta 4 and a synthetic peptide containing its actin-binding domain promote dermal wound repair in db/db diabetic mice and in aged mice," *Wound Rep. Reg.*, 11:19-24, 2003.

Safer et al., "Thymosin beta 4 and Fx, an actin-sequestering peptide, are indistinguishable," *J. Biol. Chem.*, 266:4029-4032, 1991.

Sosne et al., "Thymosin beta 4 promotes corneal wound healing and decreases inflammation in vivo following alkali injury," *Exp. Eye Res.*, 74:293-299, 2002.

Srivastava and Olson, "A genetic blueprint for cardiac development," *Nature*, 407:221-226, 2000.

Sun et al., "beta-Thymosins are not simple actin monomer buffering proteins. Insights from overexpression studies," *J. Biol. Chem.*, 271:9223-9230, 1996.

Troussard et al., "Conditional knock-out of integrin-linked kinase demonstrates an essential role in protein kinase B/Akt activation," *J. Biol. Chem.*, 278:22374-22378, 2003.

Tu et al., "A new focal adhesion protein that interacts with integrin-linked kinase and regulates cell adhesion and spreading," *J. Cell Biol.*, 153:585-598, 2001.

Tu et al., "The LIM-only protein PINCH directly interacts with integrin-linked kinase and is recruited to integrin-rich sites in spreading cells," *Mol. Cell. Biol.*, 19:2425-2434, 1999.

Van den Hoff et al., "Myocardialization of the cardiac outflow tract," *Dev. Biol.*, 212:477-490, 1999.

Velyvis et al., "Solution structure of the focal adhesion adaptor PINCH LIM1 domain and characterization of its interaction with the integrin-linked kinase ankyrin repeat domain," *J. Biol. Chem.*, 276:4932-4939, 2001.

Wu, "Integrin-linked kinase and PINCH: partners in regulation of cell-extracellular matrix interaction and signal transduction," *J. Cell Sci.*, 112:4485-4489, 1999.

Yamaji et al., "A novel integrin-linked kinase-binding protein, affixin, is involved in the early stage of cell-substrate interaction," *J. Cell Biol.*, 153:1251-1264, 2001.

Zhang et al., "Assembly of the PINCH-ILK-CH-ILKBP complex precedes and is essential for localization of each component to cell-matrix adhesion sites," *J. Cell Sci.*, 115:4777-4786, 2002.

\* cited by examiner

SCREENING OF AGENTS FOR ACTIVITY AGAINST ISCHEMIC MYOCARDIAL INSULTS

The present invention claims benefit of priority to U.S. Provisional Application Ser. Nos. 60/630,602 and 60/602,884, filed Nov. 24, 2004 and Aug. 20, 2004, respectively. The entire contents of these applications are hereby incoporated by reference.

BACKGROUND OF THE INVENTION

1. Field of the Invention

The present invention relates generally to the fields of developmental biology and molecular biology. More particularly, it concerns the identification of an important signaling pathway in cardiomyocytes. Specifically, it involves the identification of ILK and Akt as targets for the modulation of therapeutic responses to ischemic myocardial insult.

2. Description of Related Art

Coronary artery disease results in acute occlusion of cardiac vessels leading to loss of dependent myocardium. Such events are one of the leading causes of death in the Western world (American Heart Assoc., 2004). Because the heart is incapable of sufficient muscle regeneration, survivors of myocardial infarctions typically develop chronic heart failure, with over ten million cases in the United States alone (American Heart Assoc., 2004). Although more commonly affecting adults, heart disease in children is the leading non-infectious cause of death in the first year of life and often involves abnormalities in cardiac cell specification, migration or surviva (Hoffman and Kaplan, 2002).

Recent evidence suggests that a population of extracardiac or intracardiac stem cells may contribute to maintenance of the cardiomyocyte population under normal circumstances (Orlic et al., 2001; Beltrami et al., 2003; Anversa and Nadal-Ginard, 2002). Although the stem cell population may maintain a delicate balance between cell death and cell renewal, it is insufficient for myocardial repair after acute coronary occlusion. Introduction of isolated stem cells may improve myocardial function (Orlic et al., 2001; Beltrami et al., 2003; Anversa and Nadal-Ginard, 2002), but this approach has been controversial (Balsam et al., 2004; Murry et al., 2004) and requires isolation of autologous stem cells or the use of donor stem cells along with immunosuppression. Technical hurdles of stem cell delivery and differentiation have thus far prevented broad clinical application of cardiac regenerative therapies.

Regulatory pathways involved in cardiac development may have utility in reprogramming cardiomyocytes to aid in cardiac repair (Srivastava and Olson, 2000). In studies of genes expressed during cardiac morphogenesis, the inventors found that the 43-amino-acid peptide thymosin β4 was expressed in the developing heart. Thymosin β4 has numerous functions, with the most prominent involving sequestration of G-actin monomers and subsequent effects on actin-cytoskeletal organization necessary for cell motility, organogenesis and other cell biological events (Safer et al., 1991; Huff et al., 2001; Sun et al., 1996). Recent domain analyses indicate that β-thymosins can affect actin assembly based on their carboxy-terminal affinity for actin (Hertzog et al., 2004). In addition to cell motility, thymosin β4 may affect transcriptional events by influencing Rho-dependent gene expression or chromatin remodelling events regulated by nuclear actin (Marinissen et al., 2004; Olave et al., 2002). Although thymosin β4 promotes skin and corneal wound healing through its effects on cell migration, angiogenesis and possibly cell survival (Malinda et al., 1999; Sosne et al., 2002; Grant et al., 1999), the precise molecular mechanism through which it functions and its potential role in solid organ wound healing remains unknown.

SUMMARY OF THE INVENTION

Thus, in accordance with the present invention, there is provided a method of screening for an inhibitor of damage associated with myocardial ischemia comprising (a) providing a cell expressing integrin-linked kinase (ILK) and/or Akt/protein kinase B (PKB); (b) treating a cell with a candidate substance; and (c) measuring the expression, activity or stability of ILK and/or Akt/PKB, wherein an increase in the expression, activity or stability of ILK and/or Akt/PKB, as compared to a cell not treated with the candidate substance, identifies the candidate substance as an inhibitor of damage associated with myocardial ischemia. The cell may be a myocyte, such as an isolated myocyte, such as a cardiomyocyte or a neonatal rat ventricular myocyte. The myocyte maybe comprised in isolated intact tissue, for example, a cardiomyocyte located in vivo in a functioning intact heart muscle, and the functioning intact heart muscle may be subjected to an ischemic event. The method may also comprise measuring toxicity to a cell or animal.

Expression may be measured using a reporter protein coding region operably linked to an ILK or Akt/PKB promoter, where the reporter protein may be luciferase, β-gal, or green fluorescent protein. Expression may be measured using hybridization of a nucleic acid probe to a target mRNA or amplified nucleic acid product. Expression may be measured by assessing protein levels, such as by immunologic detection or mass spectrometry. Activity may be measured by assessing incorporation of labeled phosphate into a target. Stability may be measured by ILK/Akt complex formation or ILK and/or Akt protein turnover.

In another embodiment, there is provided a method of preventing, treating or limiting damage from an ischemic event comprising providing to a subject an agonist of ILK and/or Akt/PKB. The ischemic event may be myocardial infarct or heart bypass surgery. The method may further comprise treating the subject with a secondardy cardiac therapy.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error in the method being employed to determine the value, or the variation that exists among study subjects.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the detailed description of specific embodiments presented herein.

FIG. 1A, Thymosin β4 mRNA transcripts at E10.5 by whole-mount in situ hybridization in frontal view. h, head; lv, left ventricle; ot, outflow tract; rv, right ventricle. FIG. 1B, FIG. 1C, Radioactive section in situ hybridization at E10.5 in transverse section through heart. Arrowhead indicates endocardial cushion (ec); at, atria. FIG. 1D, FIG. 1E, Immunohistochemistry using thymosin β4 (FIG. 1D) and muscle actin (FIG. 1E) antibodies focused on cushion cells at E11.5. TB4, thymosin β4. FIG. 1F, FIG. 1G, Expression of thymosin β4 mRNA at E11.5 in compact layer (c) of ventricles and ventricular septum (vs). Note absence in atria. FIG. 1H, FIG. 1I, Thymosin β4 protein or 4,6-diamidino-2-phenylindole (DAPI) in outflow tract myocardium by immunohistochemistry of E9.5 transverse section. nt, neural tube.

FIG. 2A, Western blot of supernatant from thymosin β4 (TB4) transfected Cos cells using thymosin β4 antibodies. FIGS. 2B-E, Immunocytochemistry using anti-phage antibody or DAPI after thymosin-β4-expressing T7 phage (FIG. 2B, FIG. 2C) or control phage (FIG. 2D, FIG. 2E) administration in the medium of embryonic cardiac explants. FIGS. 2F-I, Mouse E11.5 cardiac outflow tract explants stained with anti-muscle actin antibody (green) or DAPI (blue) after PBS (FIG. 2F, FIG. 2G) or thymosin β4 (FIG. 2H, FIG. 2I) treatment. Scale bars, 500 μm. FIG. 2J, FIG. 2K, Distance of migrating myocardial cells in E11.5 cardiac outflow tract explants (FIG. 2J, P<0.0001) or rat neonatal cardiomyocytes (FIG. 2K, P<0.03) with or without thymosin β4 treatment. FIG. 2L, Percent of embryonic endothelial cells migrating with or without thymosin β4 (P<0.01). FIG. 2M, Beating frequency of rat neonatal cardiomyocytes with or without thymosin β4. Means and standard deviation bars with 95% confidence limits are shown. Asterisk, P<0.05.

FIG. 3A, Phage display strategy for isolating thymosin β4 (TB4) interacting proteins, and ELISA confirmation of PINCH interaction. PFU, plaque-forming units. FIG. 3B, FIG. 3C, Immunoprecipitation (IP) for thymosin β4 and immunoblot (IB) for PINCH (FIG. 3B) or ILK (FIG. 3C). FIG. 3D, Immunoprecipitation of ILK and immunoblot for PINCH and thymosin β4. Cell lysate input for each protein is shown along with protein from the immunoprecipitation (output). FIG. 3E, Immunocytochemistry with anti-ILK antibody (green) and DAPI (blue) after thymosin β4 treatment of embryonic cardiac explants or C2C12 myoblasts. FIG. 3F, Western blot of C2C12 cells treated with thymosin β4 protein or transfected with thymosin-β4-expressing plasmid (TB4$^{tr}$) using antibodies for ILK, Akt, GAPDH or phospho-specific antibody to Akt-S 473. FIG. 3G, FIG. 3H, Myocardial migration (FIG. 3G) or beating frequency (FIG. 3H) of E11.5 cardiac explants induced by thymosin β4 in the presence or absence of wortmannin (Wort.). Bars indicate standard deviations with 95% confidence interval. Asterisk, P<0.05.

FIG. 4A, FIG. 4B, Representative echocardiographic M-mode images of left ventricles after coronary ligation with (FIG. 4A) or without (FIG. 4B) thymosin β4 (TB4) treatment. Two-dimensional images are shown to the right. FIG. 4C, FIG. 4D, Distribution of left ventricular fractional shortening (FS) (FIG. 4C) or ejection fraction (EF) (FIG. 4D) at 2 and 4 weeks after coronary ligation with (n=23) or without (n=22) thymosin β4 treatment. Bars indicate means. FIG. 4E, Echocardiographic measurements for intraperitoneal, intracardiac or intraperitoneal and intracardiac administration of thymosin β4 or PBS (Control) at 4 weeks. Means and standard deviations with 95% confidence limits are shown. Asterisk, P<0.0001.

FIGS. 5A-N—Thymosin β4 promotes survival and alters scar formation after coronary artery ligation in mice. FIGS. 5A-F, Representative trichrome stain of transverse heart sections at comparable levels 14 days after coronary ligation and PBS (FIG. 5A, FIG. 5B) or thymosin β4 (TB4) treatment delivered intraperitoneally (i.p.) (FIG. 5C, FIG. 5D) or intracardiac (i.c.) (FIG. 5E, FIG. 5F). FIG. 5B, FIG. 5D and FIG. 5F are higher magnifications of FIG. 5A, FIG. 5C and FIG. 5E, respectively. Collagen in scar is indicated in blue and myocytes in red. Images are typical of 20 separate animals. lv, left ventricle; rv, right ventricle. FIG. 5G, Estimated scar volume of hearts after coronary ligation and PBS or thymosin β4 treatment. Bars indicate standard deviation at 95% confidence limits. Asterisk, P<0.02. FIG. 5H, FIG. 5I, TUNEL-positive cells (bright green) 24 h after coronary ligation and thymosin β4 or PBS treatment. FIG. 5J, FIG. 5K, DAPI stain of FIG. 5H, FIG. 5I. FIG. 5L, FIG. 5M, Higher magnification of TUNEL-positive nuclei (green) double-labelled with anti-muscle actin antibody (red striations) to mark cardiomyocytes. FIG. 5N, Western blot on heart lysates after coronary ligation and treatment with PBS or thymosin β4.

DESCRIPTION OF ILLUSTRATIVE EMBODIMENTS

Figure 1:
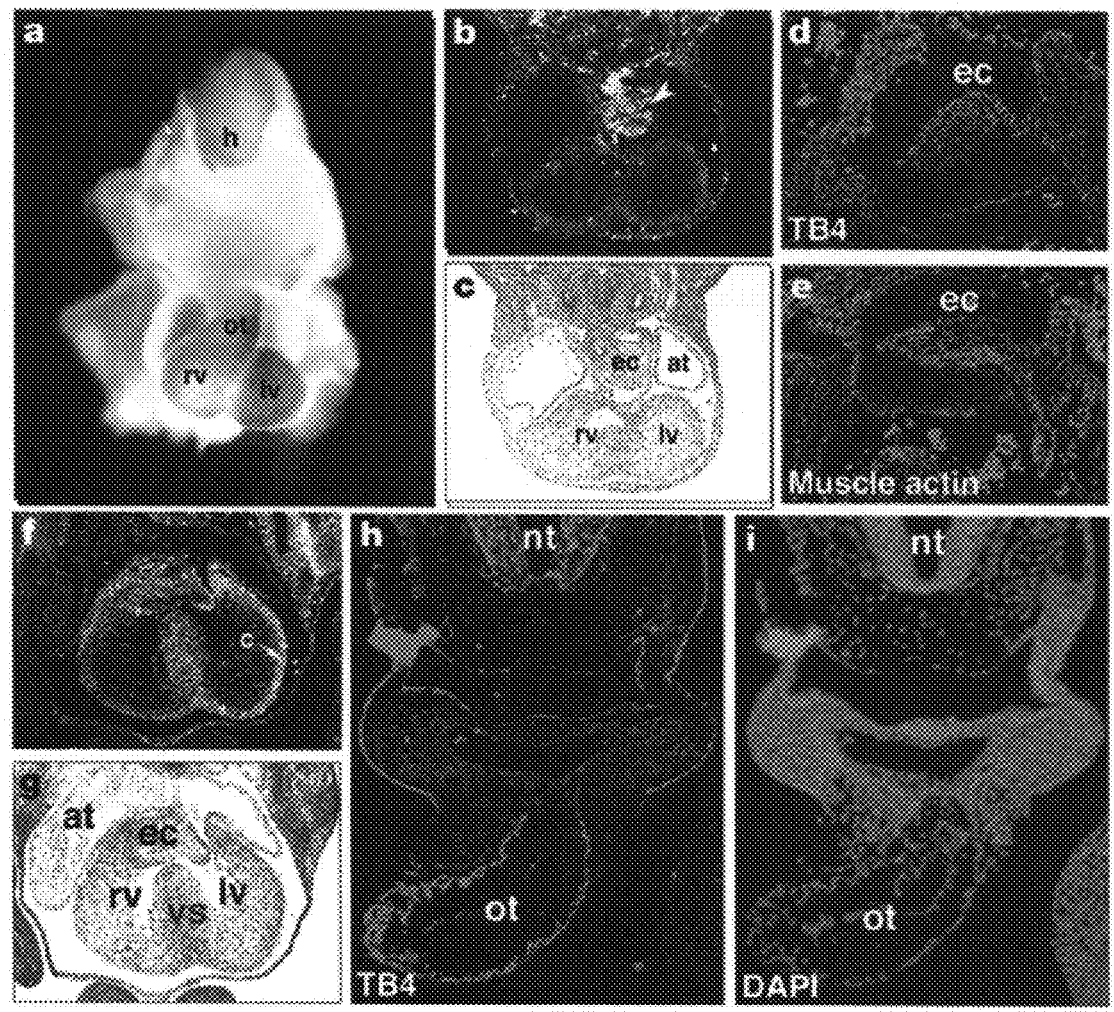
FIGS. 1A-I—Thymosin β4 is expressed in specific cardiac cell types during development.

Heart failure is one of the leading causes of morbidity and mortality in the world. In the U.S. alone, estimates indicate that 3 million people are currently living with cardiomyopathy and another 400,000 are diagnosed on a yearly basis. Dilated cardiomyopathy (DCM), also referred to as "congestive cardiomyopathy," is the most common form of the cardiomyopathies and has an estimated prevalence of nearly 40 per 100,000 individuals (Durand et al., 1995). Although there are other causes of DCM, familiar dilated cardiomyopathy has been indicated as representing approximately 20% of "idiopathic" DCM. Approximately half of the DCM cases are idiopathic, with the remainder being associated with known disease processes. For example, serious myocardial damage can result from certain drugs used in cancer chemotherapy (e.g., doxorubicin and daunoribucin), or from chronic alcohol abuse. Peripartum cardiomyopathy is another idiopathic form of DCM, as is disease associated with infectious sequelae. In sum, cardiomyopathies, including DCM, are significant public health problems.

Heart disease and its manifestations, including coronary artery disease, myocardial infarction, congestive heart failure and cardiac hypertrophy, clearly present a major health risk in the United States today. The cost to diagnose, treat and support patients suffering from these diseases is well into the billions of dollars. Two particularly severe manifestations of heart disease are myocardial infarction and cardiac hypertrophy. With respect to myocardial infarction, typically an acute thrombocytic coronary occlusion occurs in a coronary artery as a result of atherosclerosis and causes myocardial cell death. Because cardiomyocytes, the heart muscle cells, are terminally differentiated and generally incapable of cell division, they are generally replaced by scar tissue when they die during the course of an acute myocardial infarction. Scar tissue is not contractile, fails to contribute to cardiac function, and often plays a detrimental role in heart function by expanding during cardiac contraction, or by increasing the size and effective radius of the ventricle, for example, becoming hypertrophic.

The evidence presented in the present application suggests that thymosin β4, a protein involved in cell migration and survival during cardiac morphogenesis, may be re-deployed to minimize cardiomyocyte loss after cardiac infarction. Given the known roles of PINCH, ILK and Akt, the reported data are consistent with this complex having a central role in the effects of thymosin β4 on cell motility, survival and cardiac repair. The ability of thymosin β4 to prevent cell death within 24 h after coronary ligation likely leads to the decreased scar volume and improved ventricular function observed in mice. Although thymosin β4 activation of ILK is likely to have many cellular effects, the activation of Akt may be the dominant mechanism through which thymosin β4 promotes cell survival. This is consistent with Akt's proposed effect on cardiac repair when overexpressed in mouse marrow-derived stem cells administered after cardiac injury (Mangi et al., 2003), although this probably occurs in a non-cell-autonomous fashion. Whereas thymosin β4 can augment an organism's ability to heal surface wounds (Sosne et al., 2002; Grant et al., 1999; Philip et al., 2003), the work presented here is the first demonstration of thymosin β4's efficacy in healing of a solid organ, and reveals a new mechanism through which thymosin β4 affects cellular functions. Whether thymosin β4 directly affects stabilization of ILK or transcription of ILK through actin-dependent regulation of transcription factors, and which cell types are affected by these or other pathways, remain to be determined.

The early effect of thymosin β4 in protecting the heart from cell death is reminiscent of myocytes that are able to survive hypoxic insult by "hibernating" (Depre et al., 2004). Although the mechanisms underlying hibernating myocardium are unclear, alterations in metabolism and energy usage seem to promote survival of cells (Depre et al., 2004). Future studies will determine whether thymosin β4 alters cellular properties in a manner similar to hibernating myocardium, possibly allowing time for endothelial cell migration and new blood vessel formation. Given the findings here, the utility of thymosin β4 for healing after cardiac injury holds promise and warrants further pre-clinical investigation.

The present inventors thus propose that by modulating the interaction of various molecules in the pathway defined above, one can modulate the response to myocardial insults such as infarct, bypass surgery, and other potential ischemic events. In particular, the targets ILK and Akt will be assessed, and compounds that enhance their expression, stability and/or interaction will be sought.

I. Kinases

Kinases regulate many different biological processes, including cell proliferation, differentiation and signaling processes by adding phosphate groups to proteins. Uncontrolled signaling has been implicated in a variety of disease conditions, including inflammation, cancer, arteriosclerosis, psoriasis, and heart disease and hypertrophy. Reversible protein phosphorylation is the main strategy for controlling activities of eukaryotic cells. It is estimated that more than 1000 of the 10,000 proteins active in a typical mammalian cell are phosphorylated. The high-energy phosphate, which drives activation, is generally transferred from adenosine triphosphate molecules (ATP) to a particular protein by protein kinases and removed from that protein by protein phosphatases. Phosphorylation occurs in response to extracellular signals (hormones, neurotransmitters, growth and differentiation factors, etc.), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine and/or threonine residues (serine/threonine kinases, STK). A few protein kinases have dual specificity and phosphorylate threonine and tyrosine residues. Almost all kinases contain a similar 250-300 amino acid catalytic domain. The N-terminal domain, which contains subdomains I-IV, generally folds into a two-lobed structure, which binds and orients the ATP (or GTP) donor molecule. The larger C terminal lobe, which contains subdomains VI A-XI, binds the protein substrate and carries out the transfer of the γ phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contains specific residues and motifs or patterns of amino acids that are characteristic of that subdomain and are highly conserved (Hardie, and Hanks, 1995).

A. Integrin Linked Kinase

Integrin-linked kinase (ILK) was identified and cloned in 1996 based on its interaction with the β1 integrin cytoplasmic domain (Hannigan et al., 1996). It comprises three structurally distinct regions. Four ANK repeats lie at the $NH_2$ terminus of ILK. COOH-terminal to the ANK domain is a pleckstrin homology (PH)-like motif. Further downstream and partially overlapping with the PH-like motif is the COOH-terminal domain, which exhibits significant homology to other protein kinase catalytic domains. One of the key functions of ILK is to mediate protein-protein interactions. To date, nine different ILK-binding proteins have been identified, including β1 and β3 integrins, PINCH, CH-ILKPB, Affixin, Paxillin, ILKAP, PDK-1 and PKB/Akt.

The interaction between ILK and PINCH, a focal adhesion protein comprised primarily of five LIM domains (Wu, 1999), has been studied in detail. ILK forms a complex with PINCH through direct binding of the ILK $NH_2$-terminal ANK domain to the second zinc finger located within the LIM1 domain of PINCH (Li et al., 1999; Tu et al., 1999). Structural studies have revealed that many residues in this zinc finger undergo large chemical shift changes upon ILK binding (Velyvis et al., 2001), suggesting that the interaction likely involves a conformational change of the LIM1 domain.

The COOH-terminal domain of ILK interacts with the β1 integrin cytoplasmic domain (Hannigan et al., 1996) and at least three different cytoplasmic adaptor proteins. CH-ILKBP, which contains two calponin homology (CH) domains, was identified and cloned in a yeast two-hybrid screen of a human cDNA library using the ILK COOH-terminal domain as bait (Tu et al., 2001). The CH2 domain of CH-ILKBP mediates the interaction with ILK (Tu et al., 2001). Two proteins (actopaxin—Nikolopoulos and Turner, 2000—and α-parvin—Olski et al., 2001) that are closely related structurally to human CH-ILKBP have been identified independently and cloned from rat and mouse cDNA libraries, respectively. Interestingly, actopaxin was identified in a search for proteins that bind to the LD1 motif of paxillin (Nikolopoulos and Turner, 2000), and α-parvin was identified based on its sequence homology with the actin-binding domain of α-actinin (Olski et al., 2001). Although murine actopaxin and α-parvin were identified based on binding activities toward proteins other than ILK, the high degree of sequence similarity of CH-ILKBP, actopaxin, and α-parvin at both the protein level (98% identical) and the cDNA level (90% identical) suggest that the human, rat, and mouse proteins are orthologues and therefore are likely to share the ILK-binding activity. In an independent study, Yamaji et al. (2001) identified and cloned another human protein, affixin, that also binds to the ILK COOH-terminal domain. CH-ILKBP and affixin are encoded by two different genes, but they share significant sequence similarity, particularly in the CH2 domains that mediate the ILK binding, suggesting that they likely recognize a common site on ILK. Affixin is the human orthologue of mouse β-parvin, another recently described actin-binding protein (Olski et al., 2001). These recent studies define a new family of ILK-binding proteins that include CH-ILKBP-actopaxin-α-parvin and affixin-β-parvin. In addition to interacting with the CH2 domains of CH-ILKBP-actopaxin-α-parvin and affixin-β-parvin, the ILK COOH-terminal domain can also be recognized by the paxillin LD1 motif (Nikolopoulos and Turner, 2001).

Some, although probably not all, of the interactions described above occur simultaneously in cells. It has been demonstrated recently that ILK binds to PINCH and CH-ILKBP simultaneously through two separate domains (the $NH_2$-terminal ANK domain and the COOH-terminal kinase domain), resulting in the formation of a multicomponent PINCH-ILK-CH-ILKBP complex in cells (Tu et al., 2001). On the other hand, paxillin was not detected as part of the multicomponent ILK complex, despite its ability to interact with both ILK and CH-ILKBP through the LD1 motif.

B. Akt/Protein Kinase B

Akt, also known as protein kinase B (PKB), a serine/threonine kinase, is a critical enzyme in several signal transduction pathways involved in cell proliferation, apoptosis, angiogenesis, and diabetes. Four different isoforms of Akt (α, β1, β2, and γ) have been reported that differ slightly in the localization of their regulatory phosphorylation sites. Activation of Akt involves growth factor binding to a receptor tyrosine kinase and activation of PI 3-K, which phosphorylates the membrane bound $PI(4,5)P_2$ ($PIP_2$) to generate $PI(3,4,5)P_3$ ($PIP_3$). Binding of $PIP_3$ to Akt anchors it to the plasma membrane and exposes it to phosphorylation and activation by 3-phosphoinositide-dependent kinase-1 (PDK1). Akt is activated following its phosphorylation at two regulatory residues, a threonine residue on the kinase domain and a serine residue on the hydrophobic motif, which are structurally and functionally conserved within the AGC kinase family. Phosphorylation of threonine on the kinase domain, catalyzed by PDK1, is essential for Akt activation. Akt activity is augmented approximately 10-fold by phosphorylation at the serine on the hydrophobic motif by PDK2. Phosphorylation of $Thr^{308}$ and $Ser^{473}$ activates Akt a. Phosphorylation at $Thr^{309}$ and $Ser^{474}$ on Akt b1 and b2, and on $Thr^{305}$ on Akt g result in their activation. The activation of Akt is negatively regulated by PTEN, a PIP3 specific phosphatase, and SHIP, an SH2-domain containing inositol 5-phosphatase.

The principal role of Akt in the cell is to facilitate growth factor-mediated cell survival and to block apoptotic cell death. This is achieved by phosphorylating and deactivating pro-apoptotic factors such as BAD, Caspase 9, and Forkhead transcription factors (FKHR). The phosphorylation of BAD allows it to bind to 14-3-3 protein thereby preventing localization of BAD at the mitochondria to induce apoptosis. Additionally, phosphorylation of FKHR by Akt prevents it from transcribing Fas ligand; hence it promotes cell survival. Akt also phosphorylates and activates IKKa, which leads to NF-kB activation and cell survival. Akt is also known to stimulate glycogen synthesis by phosphorylating and inactivating GSK-3 leading to the activation of glycogen synthase. The inactivation of GSK-3 also induces the up-regulation of cyclin D, which enhances cell cycle progression.

Akt is reported to play a critical role in tumorigenesis, becoming activated when tumor suppressors such as $p27^{Kip1}$ and PTEN lose their functions. Phosphorylation of p27 at $Thr^{157}$ by Akt impairs its nuclear import and leads to its cytoplasmic accumulation. Cytoplasmic mislocalization of p27 has been strongly linked to loss of differentiation and poor outcome in breast cancer patients. Akt can also physically associate with endogenous p21, a cell cycle inhibitor, and phosphorylate it at $Thr^{145}$, causing its localization to the cytoplasm, ultimately resulting in deregulation of cell proliferation.

II. Methods of Treating Heart Failure and Cardiac Hypertrophy

Heart failure of some forms may be curable and these are dealt with by treating the primary disease, such as anemia or thyrotoxicosis. Also curable are forms caused by anatomical problems, such as a heart valve defect. These defects can be surgically corrected. However, for the most common forms of heart failure—those due to damaged heart muscle—no known cure exists. Treating the symptoms of these diseases helps, and some treatments of the disease have been successful. The treatments attempt to improve patients' quality of life and length of survival through lifestyle change and drug therapy. Patients can minimize the effects of heart failure by controlling the risk factors for heart disease, but even with lifestyle changes, most heart failure patients must take medication, often two or more drugs daily.

Several types of drugs have proven useful in the treatment of heart failure: diuretics help reduce the amount of fluid in the body and are useful for patients with fluid retention and hypertension; and digitalis can be used to increase the force of the heart's contractions, helping to improve circulation. Results of recent studies have placed more emphasis on the use of ACE inhibitors (Manoria and Manoria, 2003). Several large studies have indicated that ACE inhibitors improve survival among heart failure patients and may slow, or perhaps even prevent, the loss of heart pumping activity (for a review see De Feo et al., 2003; DiBianco, 2003).

Patients who cannot take ACE inhibitors may receive a nitrate and/or a drug called hydralazine, each of which helps relax tension in blood vessels to improve blood flow (Ahmed, 2003).

Heart failure is almost always life-threatening. When drug therapy and lifestyle changes fail to control its symptoms, a heart transplant may be the only treatment option. However, candidates for transplantation often have to wait months or even years before a suitable donor heart is found. Recent studies indicate that some transplant candidates improve during this waiting period through drug treatment and other therapy, and can be removed from the transplant list (Conte et al., 1998).

Transplant candidates who do not improve sometimes need mechanical pumps, which are attached to the heart. Called left ventricular assist devices (LVADs), the machines take over part or virtually all of the heart's blood-pumping activity. However, current LVADs are not permanent solutions for heart failure but are considered bridges to transplantation.

As a final alternative, there is an experimental surgical procedure for severe heart failure available called cardiomyoplasty (Dumcius et al., 2003). This procedure involves detaching one end of a muscle in the back, wrapping it around the heart, and then suturing the muscle to the heart. An implanted electric stimulator causes the back muscle to contract, pumping blood from the heart. To date, none of these treatments have been shown to cure heart failure, but can at least improve quality of life and extend life for those suffering this disease.

A. Pharmaceutical Inhibitors

The present invention proposes the use of proteins, nucleic acids and small molecules to intervene in the pathway involving ILK and Akt. The goal of such therapies is to increase the expression, stability and/or interaction of ILK and Akt. Methods for the identification of such agents are provided herein, and methods of their use in therapy will follow standard procedures of other cardiotherapeutic drugs.

B. Vectors for Cloning, Gene Transfer and Expression

Within certain embodiments of the present inventin, expression vectors expression ILK and/or Akt may be used to treat or prevent the effects of myocardial ischemia. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

i. Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In certain embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best-known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

In certain embodiments, the native PRK promoter will be employed to drive expression of either the corresponding PRK gene, a heterologous PRK gene, a screenable or selectable marker gene, or any other gene of interest.

In other embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 1 and 2 list several regulatory elements that may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 1 and Table 2). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 1

Promoter and/or Enhancer

| Promoter/Enhancer | References |
| --- | --- |
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987a |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |

TABLE 1-continued

Promoter and/or Enhancer

| Promoter/Enhancer | References |
| --- | --- |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
| --- | --- | --- |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

Of particular interest are muscle specific promoters, and more particularly, cardiac specific promoters. These include the myosin light chain-2 promoter (Franz et al., 1994; Kelly et al., 1995), the alpha actin promoter (Moss et al., 1996), the troponin 1 promoter (Bhavsar et al., 1996); the $Na^+/Ca^{2+}$ exchanger promoter (Barnes et al., 1997), the dystrophin promoter (Kimura et al., 1997), the alpha7 integrin promoter (Ziober & Kramer, 1996), the brain natriuretic peptide promoter (LaPointe et al., 1996) and the alpha B-crystallin/small heat shock protein promoter (Gopal-Srivastava, 1995), alpha myosin heavy chain promoter (Yamauchi-Takihara et al., 1989) and the ANF promoter (LaPointe et al., 1988).

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

ii. Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

iii. Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

iv. Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kB, linear, double-stranded DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Racher et al. (1995) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors, as described by Karlsson et al. (1986), or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$-$10^{12}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1991). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful (Wong et al., 1980). demonstrated the feasibility of liposome-mediated delivery and expression of foreign DNA in cultured chick embryo, HeLa and hepatoma cells (Nicolau et al., 1987). accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs that can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type by any number of receptor-ligand systems with or without liposomes. For example, epidermal growth factor (EGF) may be used as the receptor for mediated delivery of a nucleic acid into cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

v. Combined Therapy

In another embodiment, it is envisioned to use an agent that increases the expression, stability and/or interaction of ILK and/or Akt in combination with other therapeutic modalities. Thus, in addition to the therapies described above, one may also provide to the patient more "standard" pharmaceutical cardiac therapies. Examples of other therapies include, without limitation, so-called "beta blockers," anti-hypertensives, cardiotonics, anti-thrombotics, vasodilators, hormone antagonists, iontropes, diuretics, endothelin antagonists, calcium channel blockers, phosphodiesterase inhibitors, ACE inhibitors, angiotensin type 2 antagonists and cytokine blockers/inhibitors, and HDAC inhibitors.

Combinations may be achieved by contacting cardiac cells with a single composition or pharmacological formulation that includes both agents, or by contacting the cell with two distinct compositions or formulations, at the same time, wherein one composition includes the expression construct and the other includes the agent. Alternatively, the therapy using the ILK/Akt agonist may precede or follow administration of the other agent(s) by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the ILK/Akt agonist, or the other agent will be desired. In this regard, various combinations may be employed. By way of illustration, where the ILK/Akt agonist is "A" and the other agent is "B," the following permutations based on 3 and 4 total administrations are exemplary:

| A/B/A | B/A/B | B/B/A | A/A/B | B/A/A | A/B/B | B/B/B/A | B/B/A/B |
|-------|-------|-------|-------|-------|-------|---------|---------|
| A/A/B/B | A/B/A/B | A/B/B/A | B/B/A/A | B/A/B/A | B/A/A/B | B/B/B/A |
| A/A/A/B | B/A/A/A | A/B/A/A | A/A/B/A | A/B/B/B | B/A/B/B | B/B/A/B |

Other combinations are likewise contemplated.

D. Adjunct Therapeutic Agents

Pharmacological therapeutic agents and methods of administration, dosages, etc., are well known to those of skill in the art (see for example, the "Physicians Desk Reference," Goodman & Gilman's "The Pharmacological Basis of Therapeutics," "Remington's Pharmaceutical Sciences," and "The Merck Index, Thirteenth Edition," incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject, and such invidual determinations are within the skill of those of ordinary skill in the art.

Non-limiting examples of a pharmacological therapeutic agent that may be used in the present invention include an antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof.

In addition, it should be noted that any of the following may be used to develop new sets of cardiac therapy target genes as β-blockers were used in the present examples (see below). While it is expected that many of these genes may overlap, new gene targets likely can be developed.

i. Antihyperlipoproteinemics

In certain embodiments, administration of an agent that lowers the concentration of one of more blood lipids and/or lipoproteins, known herein as an "antihyperlipoproteinemic," may be combined with a cardiovascular therapy according to the present invention, particularly in treatment of atherosclerosis and thickenings or blockages of vascular tissues. In certain aspects, an antihyperlipoproteinemic agent may comprise an aryloxyalkanoic/fibric acid derivative, a resin/bile acid sequesterant, a HMG CoA reductase inhibitor, a nicotinic acid derivative, a thyroid hormone or thyroid hormone analog, a miscellaneous agent or a combination thereof.

a. Aryloxyalkanoic Acid/Fibric Acid Derivatives

Non-limiting examples of aryloxyalkanoic/fibric acid derivatives include beclobrate, enzafibrate, binifibrate, ciprofibrate, clinofibrate, clofibrate (atromide-S), clofibric acid, etofibrate, fenofibrate, gemfibrozil (lobid), nicofibrate, pirifibrate, ronifibrate, simfibrate and theofibrate.

b. Resins/Bile Acid Sequesterants

Non-limiting examples of resins/bile acid sequesterants include cholestyramine (cholybar, questran), colestipol (colestid) and polidexide.

c. HMG CoA Reductase Inhibitors

Non-limiting examples of HMG CoA reductase inhibitors include lovastatin (mevacor), pravastatin (pravochol) or simvastatin (zocor).

d. Nicotinic Acid Derivatives

Non-limiting examples of nicotinic acid derivatives include nicotinate, acepimox, niceritrol, nicoclonate, nicomol and oxiniacic acid.

e. Thryroid Hormones and Analogs

Non-limiting examples of thyroid hormones and analogs thereof include etoroxate, thyropropic acid and thyroxine.

f. Miscellaneous Antihyperlipoproteinemics

Non-limiting examples of miscellaneous antihyperlipoproteinemics include acifran, azacosterol, benfluorex, b-benzalbutyramide, camitine, chondroitin sulfate, clomestrone, detaxtran, dextran sulfate sodium, 5,8,11,14,17-eicosapentaenoic acid, eritadenine, furazabol, meglutol, melinamide, mytatrienediol, ornithine, g-oryzanol, pantethine, pentaerythritol tetraacetate, a-phenylbutyramide, pirozadil, probucol (lorelco), b-sitosterol, sultosilic acid-piperazine salt, tiadenol, triparanol and xenbucin.

ii. Antiarteriosclerotics

Non-limiting examples of an antiarteriosclerotic include pyridinol carbamate.

iii. Antithrombotic/Fibrinolytic Agents

In certain embodiments, administration of an agent that aids in the removal or prevention of blood clots may be combined with administration of a modulator, particularly in treatment of atherosclerosis and vasculature (e.g., arterial) blockages. Non-limiting examples of antithrombotic and/or fibrinolytic agents include anticoagulants, anticoagulant antagonists, antiplatelet agents, thrombolytic agents, thrombolytic agent antagonists or combinations thereof.

In certain aspects, antithrombotic agents that can be administered orally, such as, for example, aspirin and wafarin (coumadin), are preferred.

a. Anticoagulants

A non-limiting example of an anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin.

b. Antiplatelet Agents

Non-limiting examples of antiplatelet agents include aspirin, a dextran, dipyridamole (persantin), heparin, sulfinpyranone (anturane) and ticlopidine (ticlid).

c. Thrombolytic Agents

Non-limiting examples of thrombolytic agents include tissue plasminogen activator (activase), plasmin, pro-urokinase, urokinase (abbokinase) streptokinase (streptase), anistreplase/APSAC (eminase).

iv. Blood Coagulants

In certain embodiments wherein a patient is suffering from a hemhorrage or an increased likelyhood of hemhorraging, an agent that may enhance blood coagulation may be used. Non-limiting examples of a blood coagulation promoting agent include thrombolytic agent antagonists and anticoagulant antagonists.

a. Anticoagulant Antagonists

Non-limiting examples of anticoagulant antagonists include protamine and vitamine K1.

b. Thrombolytic Agent Antagonists and Antithrombotics

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

v. Antiarrhythmic Agents

Non-limiting examples of antiarrhythmic agents include Class I antiarrhythmic agents (sodium channel blockers), Class II antiarrhythmic agents (beta-adrenergic blockers), Class II antiarrhythmic agents (repolarization prolonging drugs), Class IV antiarrhythmic agents (calcium channel blockers) and miscellaneous antiarrhythmic agents.

a. Sodium Channel Blockers

Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocainide (tonocard) and mexiletine (mexitil). Non-limiting examples of Class IC antiarrhythmic agents include encainide (enkaid) and flecainide (tambocor).

b. Beta Blockers

Non-limiting examples of a beta blocker, otherwise known as a b-adrenergic blocker, a b-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol.

c. Repolarization Prolonging Agents

Non-limiting examples of an agent that prolong repolarization, also known as a Class III antiarrhythmic agent, include amiodarone (cordarone) and sotalol (betapace).

d. Calcium Channel Blockers/Antagonist

Non-limiting examples of a calcium channel blocker, otherwise known as a Class IV antiarrhythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexiline. In certain embodiments a calcium channel blocker comprises a long-acting dihydropyridine (amlodipine) calcium antagonist.

e. Miscellaneous Antiarrhythmic Agents

Non-limiting examples of miscellaneous antiarrhymic agents include adenosine (adenocard), digoxin (lanoxin), acecainide, ajmaline, amoproxan, aprindine, bretylium tosylate, bunaftine, butobendine, capobenic acid, cifenline, disopyramide, hydroquinidine, indecainide, ipatropium bromide, lidocaine, lorajmine, lorcainide, meobentine, moricizine, pirmenol, prajmaline, propafenone, pyrinoline, quinidine polygalacturonate, quinidine sulfate and viquidil.

vi. Antihypertensive Agents

Non-limiting examples of antihypertensive agents include sympatholytic, alpha/beta blockers, alpha blockers, anti-angiotensin II agents, beta blockers, calcium channel blockers, vasodilators and miscellaneous antihypertensives.

a. Alpha Blockers

Non-limiting examples of an alpha blocker, also known as an a-adrenergic blocker or an a-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin.

b. Alpha/Beta Blockers

In certain embodiments, an antihypertensive agent is both an alpha and beta adrenergic antagonist. Non-limiting examples of an alpha/beta blocker comprise labetalol (normodyne, trandate).

c. Anti-Angiotension II Agents

Non-limiting examples of anti-angiotension II agents include include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan.

d. Sympatholytics

Non-limiting examples of a sympatholytic include a centrally acting sympatholytic or a peripherially acting sympatholytic. Non-limiting examples of a centrally acting sympatholytic, also known as an central nervous system (CNS)

sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin).

e. Vasodilators

In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(b-diethylaminoethyl ether), hexobendine, itramin tosylate, khellin, lidoflanine, mannitol hexanitrane, medibazine, nicorglycerin, pentaerythritol tetranitrate, pentrinitrol, perhexiline, pimethylline, trapidil, tricromyl, trimetazidine, troInitrate phosphate and visnadine.

In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

f. Miscellaneous Antihypertensives

Non-limiting examples of miscellaneous antihypertensives include ajmaline, g aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quantemary ammonium compound, a reserpine derivative or a suflonamide derivative.

Arylethanolamine Derivatives. Non-limiting examples of arylethanolamine derivatives include amosulalol, bufuralol, dilevalol, labetalol, pronethalol, sotalol and sulfinalol.

Benzothiadiazine Derivatives. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide.

N-carboxyalkyl(peptide/lactam) Derivatives. Non-limiting examples of N-carboxyalkyl(peptide/lactam) derivatives include alacepril, captopril, cilazapril, delapril, enalapril, enalaprilat, fosinopril, lisinopril, moveltipril, perindopril, quinapril and ramipril.

Dihydropyridine Derivatives. Non-limiting examples of dihydropyridine derivatives include amlodipine, felodipine, isradipine, nicardipine, nifedipine, nilvadipine, nisoldipine and nitrendipine.

Guanidine Derivatives. Non-limiting examples of guanidine derivatives include bethanidine, debrisoquin, guanabenz, guanacline, guanadrel, guanazodine, guanethidine, guanfacine, guanochlor, guanoxabenz and guanoxan.

Hydrazines/Phthalazines. Non-limiting examples of hydrazines/phthalazines include budralazine, cadralazine, dihydralazine, endralazine, hydracarbazine, hydralazine, pheniprazine, pildralazine and todralazine.

Imidazole Derivatives. Non-limiting examples of imidazole derivatives include clonidine, lofexidine, phentolamine, tiamenidine and tolonidine.

Quanternary Ammonium Compounds. Non-limiting examples of quantemary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate.

Reserpine Derivatives. Non-limiting examples of reserpine derivatives include bietaserpine, deserpidine, rescinnamine, reserpine and syrosingopine.

Suflonamide Derivatives. Non-limiting examples of sulfonamide derivatives include ambuside, clopamide, furosemide, indapamide, quinethazone, tripamide and xipamide.

vii. Vasopressors

Vasopressors generally are used to increase blood pressure during shock, which may occur during a surgical procedure. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

viii. Treatment Agents for Congestive Heart Failure

Non-limiting examples of agents for the treatment of congestive heart failure include anti-angiotension II agents, afterload-preload reduction treatment, diuretics and inotropic agents.

a. Afterload-Preload Reduction

In certain embodiments, an animal patient that can not tolerate an angiotension antagonist may be treated with a combination therapy. Such therapy may combine adminstration of hydralazine (apresoline) and isosorbide dinitrate (isordil, sorbitrate).

b. Diuretics

Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furterene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetamide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretamide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexiline, ticmafen and urea.

c. Inotropic Agents

Non-limiting examples of a positive inotropic agent, also known as a cardiotonic, include acefylline, an acetyldigitoxin, 2-amino-4-picoline, amrinone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol.

In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include anrinone (inocor).

d. Antianginal Agents

Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

E. Surgical Therapeutic Agents

In certain aspects, the secondary therapeutic agent may comprise a surgery of some type, which includes, for example, preventative, diagnostic or staging, curative and palliative surgery. Surgery, and in particular a curative surgery, may be used in conjunction with other therapies, such as the present invention and one or more other agents.

Such surgical therapeutic agents for vascular and cardiovascular diseases and disorders are well known to those of skill in the art, and may comprise, but are not limited to, performing surgery on an organism, providing a cardiovascular mechanical prostheses, angioplasty, coronary artery reperfusion, catheter ablation, providing an implantable cardioverter defibrillator to the subject, mechanical circulatory support or a combination thereof. Non-limiting examples of a mechanical circulatory support that may be used in the present invention comprise an intra-aortic balloon counterpulsation, left ventricular assist device or combination thereof.

F. Drug Formulations and Routes for Administration to Patients

It will be understood that in the discussion of formulations and methods of treatment, references to any compounds are meant to also include the pharmaceutically acceptable salts, as well as pharmaceutical compositions. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector or cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the vectors or cells of the compositions.

In specific embodiments of the invention the pharmaceutical formulation will be formulated for delivery via rapid release, other embodiments contemplated include but are not limited to timed release, delayed release, and sustained release. Formulations can be an oral suspension in either the solid or liquid form. In further embodiments, it is contemplated that the formulation can be prepared for delivery via parenteral delivery, or used as a suppository, or be formulated for subcutaneous, intravenous, intramuscular, intraperitoneal, sublingual, transdermal, or nasopharyngeal delivery.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256, 108; 4,166,452; and 4,265,874 to form osmotic therapeutic tablets for control release (hereinafter incorporated by reference).

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain an active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. Pharmaceutical compositions may be in the form of a sterile injectable aqueous or oleagenous suspension. Suspensions may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds may also be administered in the form of suppositories for rectal administration of the drug. These compositions can be prepared by mixing a therapeutic agent with a suitable non-irritating excipient that is solid at ordinary temperatures, but liquid at the rectal temperature and will therefore melt in the rectum to release the drug. Such materials are cocoa butter and polyethylene glycols.

For topical use, creams, ointments, jellies, gels, epidermal solutions or suspensions, etc., containing a therapeutic compound are employed. For purposes of this application, topical application shall include mouthwashes and gargles.

Formulations may also be administered as nanoparticles, liposomes, granules, inhalants, nasal solutions, or intravenous admixtures The previously mentioned formulations are all contemplated for treating patients suffering from heart failure or hypertrophy.

The amount of active ingredient in any formulation may vary to produce a dosage form that will depend on the particular treatment and mode of administration. It is further understood that specific dosing for a patient will depend upon a variety of factors including age, body weight, general health, sex, diet, time of administration, route of administration, rate of excretion, drug combination and the severity of the particular disease undergoing therapy.

III. Screening Methods

The present invention further comprises methods for identifying ILK/Akt agonists that are useful in the prevention or treatment or reversal of myocardial ischemic disease states. These assays may comprise random screening of large libraries of candidate substances; alternatively, the assays may be used to focus on particular classes of compounds selected with an eye towards structural attributes that are believed to make them more likely to augment ILK/Akt activity.

To identify an agonist of ILK, Akt or their complex, one generally will determine the expression, activity or stability of the individual kinases alone, or their complexed activity. Assays may be cell free, but also may be conducted in isolated cells, organs, or in living organisms. Typically, kinase activity is measured by providing an unnphosphorylated target and measuring the amount of labeled phosphate added.

It will, of course, be understood that all the screening methods of the present invention are useful in themselves notwithstanding the fact that effective candidates may not be found. The invention provides methods for screening for such candidates, not solely methods of finding them.

A. Modulators

As used herein the term "candidate substance" refers to any molecule that may potentially increase the activity or functions of ILK and/or Akt. The candidate substance may be a protein or fragment thereof, a small molecule, or even a nucleic acid. It may prove to be the case that the most useful pharmacological compounds will be compounds that are structurally related to known agonists. Using lead compounds to help develop improved compounds is known as "rational drug design" and includes not only comparisons with know inhibitors and activators, but predictions relating to the structure of target molecules.

The goal of rational drug design is to produce structural analogs of biologically active polypeptides or target compounds. By creating such analogs, it is possible to fashion drugs that are more active or stable than the natural molecules, which have different susceptibility to alteration, or which may affect the function of various other molecules. In one approach, one would generate a three-dimensional structure for a target molecule, or a fragment thereof. This could be accomplished by x-ray crystallography, computer modeling, or by a combination of both approaches.

It also is possible to use antibodies to ascertain the structure of a target compound, activator, or inhibitor. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecular libraries that are believed to meet the basic criteria for useful drugs in an effort to "brute force" the identification of useful compounds. Screening of such libraries, including combinatorially-generated libraries (e.g., peptide libraries), is a rapid and efficient way to screen large number of related (and unrelated) compounds for activity. Combinatorial approaches also lend themselves to rapid evolution of potential drugs by the creation of second, third, and fourth generation compounds modeled on active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. Such compounds are described in greater detail elsewhere in this document.

For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

B. In Vitro Assays

A quick, inexpensive and easy assay to run is an in vitro assay. Such assays generally use isolated molecules and can be run quickly and in large numbers, thereby increasing the amount of information obtainable in a short period. A variety of vessels may be used to run the assays, including test tubes, plates, dishes and other surfaces such as dipsticks or beads. The assay may look at the phosphorylation of substrates, or it may look at a more global function.

A technique for high throughput screening of compounds is described in WO 84/03564. Large numbers of small peptide test compounds are synthesized on a solid substrate, such as plastic pins or some other surface. Such peptides could be rapidly screening for their ability to bind and inhibit PRK.

C. In Cyto Assays

The present invention also contemplates the screening of compounds for their ability to modulate ILK and/or Akt in cells. Various cell lines can be utilized for such screening assays, including cells specifically engineered for this purpose. For example, ILK and/or Akt promoters maybe linked to screenable or selectable markers, and the candidate substance may be assessed for its ability to increase expression of the marker.

D. In Vivo Assays

In vivo assays involve the use of various animal models of ischemic heart disease, including transgenic animals, that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for inhibitors may be conducted using an animal model derived from any of these species.

Treatment of animals with test compounds will involve the administration of the compound, in an appropriate form, to the animal. Administration will be by any route that could be utilized for clinical purposes. Determining the effectiveness of a compound in vivo may involve a variety of different criteria. Also, measuring toxicity and dose response can be performed in animals in a more meaningful fashion than in in vitro or in cyto assays.

E. Immunologic Detection

Thus, in accordance with the present invention, methods are provided for the assaying of ILK and Akt/PKB protein expression. There are a variety of methods that can be used to assess protein expression. One such approach is to perform protein identification with the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (see, e.g., Antibodies: A Laboratory Manual, Cold Spring Harbor Laboratory, 1988; incorporated herein by reference).

In particular, antibodies to calcyclin, calpactin I light chain, astrocytic phosphoprotein PEA-15 and tubulin-specific chaperone A are contemplated.

In accordance with the present invention, immunodetection methods are provided. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle & Ben-Zeev O, 1999; Gulbis & Galand, 1993; De Jager et al., 1993; and Nakamura et al., 1987, each incorporated herein by reference. In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

F. Mass Spectrometry

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that are useful in assessing ILK and/or Akt expression.

i. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 μL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

ii. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

iii. SIMS

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

iv. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

v. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modern commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

G. Nucleic Acid Detection

In alternative embodiments for detecting protein expression, one may assay for gene transcription. For example, an indirect method for detecting protein expression is to detect mRNA transcripts from which the proteins are made. The following is a discussion of such methods, which are applicable particularly to calcyclin, calpactin I light chain, astrocytic phosphoprotein PEA-15 and tubulin-specific chaperone A in the context of the present invention.

i. Hybridization

There are a variety of ways by which one can assess gene expression. These methods either look at protein or at mRNA levels. Methods looking at mRNAs all fundamentally rely, at a basic level, on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

ii. Amplification of Nucleic Acids

Since many mRNAs are present in relatively low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Inis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Whereas standard PCR usually uses one pair of primers to amplify a specific sequence, multiplex-PCR (MPCR) uses multiple pairs of primers to amplify many sequences simultaneously (Chamberlan et al., 1990). The presence of many PCR primers in a single tube could cause many problems, such as the increased formation of misprimed PCR products and "primer dimers", the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR products, etc.) caused during MPCR, there is a limit (less than 20) to the number of primers that can be used in a MPCR reaction. See also European Application No. 0 364 255 and Mueller & Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

iii. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

iv. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phosphorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

IV. EXAMPLES

The following examples are included to further illustrate various aspects of the invention. It should be appreciated by those of skill in the art that the techniques disclosed in the examples which follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

RNA in situ hybridization. Whole-mount or section RNA in situ hybridization of E9.5-E12.5 mouse embryos was performed with digoxigenin-labelled or $^{35}$S-labelled antisense riboprobes synthesized from the 3' untranslated region of mouse thymosin β4 cDNA that did not share homology with the closely related transcript of thymosin β10, as previously described (Yamagishi et al., 2003).

Immunohistochemistry. Embryonic or adult cardiac tissue was embedded in paraffin and sections used for immunohistochemistry. Embryonic heart sections were incubated with anti-thymosin β4 (a gift of H. Yin) that does not recognize thymosin β10 (Yu et al., 1993). Adult hearts were sectioned at ten equivalent levels from the base of the heart to the apex. Serial sections were used for trichrome sections and reaction with muscle actin, c-kit, Sca-1, Abcg2 and BrdU antibodies and for TUNEL assay (Intergen Company S7111).

Collagen gel migration assay. Outflow tract was dissected from E11.5 wild-type mouse embryos and placed on collagen matrices as previously described (Runyan and Markwald, 1983. After 10 h of attachment explants were incubated in 30 ng per 300 μl thymosin β4 in PBS, PBS alone or thymosin β4 and 100 nM wortmannin. Cultures were carried out for 3-9 days at 37° C. 5% $CO_2$ and fixed in 4% paraformaldehyde in PBS for 10 min at room temperature. Cells were counted for quantification of migration and distance using at least three separate explants under each condition for endothelial migration and eight separate explants for myocardial migration.

Immunocytochemistry on collagen gel explants. Paraformaldehyde-fixed explants were permeabilized for 10 min at room temperature with Permeabilize solution (10 mM PIPES pH 6.8; 50 mM NaCl, 0.5% Triton X-100, 300 mM sucrose, 3 mM $MgCl_2$) and rinsed with PBS twice for 5 min each at room temperature. After a series of blocking and rinsing steps, detection antibodies were used and explants rinsed and incubated with equilibration buffer (Anti-Fade kit) for 10 min at room temperature. Explants were scooped to a glass microscope slide, covered and examined by fluorescein microscopy. TUNEL assay was performed using ApopTag plus fluorescein in situ apoptosis detection kit (Intergen Company S7111) as recommended.

Embryonic T7 phage display cDNA library and phage biopanning. Equal amounts of messenger RNA were isolated and purified from E9.5-E12.5 mouse embryonic hearts by using Straight A's mRNA Isolation System (Novagen). cDNA was synthesized by using T7Select10-3 OrientExpress cDNA Random Primer Cloning System (Novagen). The vector T7Select10-3 was used to display random-primed cDNA at the C terminus of 5-15 phage 10B coat protein molecules. $10^9$ plaque-forming units of the T7 phage embryonic heart library (100× of the complexity) in 500 μl of PBST was applied to a column of Affi-gel bound to thymosin β4 to achieve low-stringency biopanning to identify thymosin β4 interacting partners. See Supplementary Methods for details of phage packaging, phage biopanning and ELISA confirmation.

Co-immunoprecipitation. Cos and 10T1/2 cells were transfected with thymosin β4, PINCH and/or ILK and lysates precipitated with antibodies to each as previously described (Garg et al., 2003). Western blots were performed using anti-ILK polyclonal antibody (Santa Cruz), anti-thymosin β4 polyclonal antibody (Yu et al., 1993) (gift of H. Yin) and anti-Myc or anti-Flag antibody against tagged versions of PINCH.

Animals and surgical procedures. Myocardial infarction was produced in 58 male C57BL/6J mice at 16 weeks of age (25-30 g) by ligation of the left anterior descending coronary artery as previously described (Garner et al., 2003). All animal protocols were reviewed and approved by the University of Texas Southwestern Medical Center Institutional Animal Care Advisory Committee and were in compliance with the rules governing animal use as published by the NIH. Twenty-nine of the ligated mice received thymosin β4 treatment immediately after ligation and the remaining 29 received PBS injections. Treatment was given intracardiac with thymosin β4 (200 ng in 10 μl collagen) or with 10 μl of collagen; intraperitoneally with thymosin β4 (150 μg in 300 μl PBS) or with 300 μl of PBS; or by both intracardiac and intraperitoneal injections. Intraperitoneal injections were given every 3 days until mice were killed. Doses were based on previous studies of thymosin β4 biodistribution (Mora et al., 1997). Hearts were removed, weighed and fixed for histological sectioning. Additional mice were operated on in a similar fashion for studies 0.5, 1, 3, 6 and 11 days after ligation.

Analysis of cardiac function by echocardiography. Echocardiograms to assess systolic function were performed using M-mode and two-dimensional measurements as described previously (Garner et al., 2003). The measurements represented the average of six selected cardiac cycles from at least two separate scans performed in random-blind fashion with papillary muscles used as a point of reference for consistency in level of scan. End diastole was defined as the maximal left ventricle diastolic dimension and end systole was defined as the peak of posterior wall motion. Single outliers in each group were omitted for statistical analysis. Fractional shortening (FS), a surrogate of systolic function, was calculated from left ventricle dimensions as follows:

$$FS=((EDD-ESD)/EDD) \times 100\%.$$ Ejection fraction (EF) was calculated from two-dimensional images.

Calculation of scar volume. Scar volume was calculated using six sections through the heart of each mouse using Openlab 3.03 software (Improvision) similar to that previously described (Balsam et al., 2004). Percent area of collagen deposition was measured on each section in a blinded fashion and averaged for each mouse.

Statistical analyses. Statistical calculations were performed using a standard t-test of variables with 95% confidence intervals.

Example 2

Results

Developmental expression of thymosin β4. Expression of thymosin β4 in the developing brain was previously reported (Lin and Morrison-Bogorad, 1990), as was expression in the cardiovascular system (Gomez-Marquez et al., 1996), although not in significant detail. Whole-mount RNA in situ hybridization of embryonic day (E)10.5 mouse embryos revealed thymosin β4 expression in the left ventricle, outer curvature of the right ventricle and cardiac outflow tract (FIG. 1A). Radioactive in situ hybridization indicated that thymosin β4 transcripts were enriched in the region of cardiac valve precursors known as endocardial cushions (FIG. 1B, 1C). Cells in this region are derived from endothelial cells that undergo mesenchymal transformation and invade a swelling of extracellular matrix separating the myocardium and endocardium. The inventors found that thymyosin-β4-expressing cells in the cushions (FIG. 1D) co-expressed cardiac muscle actin (FIG. 1E), suggesting that thymosin β4 was present in migratory cardiomyocytes known to invade the endocardial cushion (Van den Hoff et al., 1999). Thymosin β4 transcripts and protein were also expressed at E9.5-E11.5 in the ventricular septum and the more proliferative region of the myocardium, known as the compact layer, which migrates into the trabecular region as the cells mature (FIG. 1F, 1G). Finally, outflow tract myocardium that migrates from a secondary heart field also expressed high levels of thymosin β4 protein (Kelly and Buckingham, 2002) (FIG. 1H, 1I).

Secreted thymosin β4 stimulates cardiac cell migration and survival. Although thymosin β4 is found in the cytosol and nucleus and functions intracellularly (Huff et al., 2001), the inventors found that conditioned medium of Cos1 cells transfected with Myc-tagged thymosin β4 contained thymosin β4 detectable by western blot (FIG. 2A), consistent with previous reports of thymosin β4 secretion and presence in wound fluid (Grant et al., 1999; Frohm et al., 1996; Huang and Wang, 2001). Upon expression of thymosin β4 on the surface of phage particles added extracellularly to embryonic cardiac explants, the inventors found that an anti-phage antibody coated the cell surface and was ultimately detected intracellularly in the cytosol and nucleus, whereas control phage was not detectable (FIGS. 2B-E). Similar observations were made using biotinylated thymosin β4 (data not shown). These data indicated that secreted thymosin β4 was internalized into cells, as previously suggested, although the mechanism of cellular entry remains to be determined.

Figure 2:
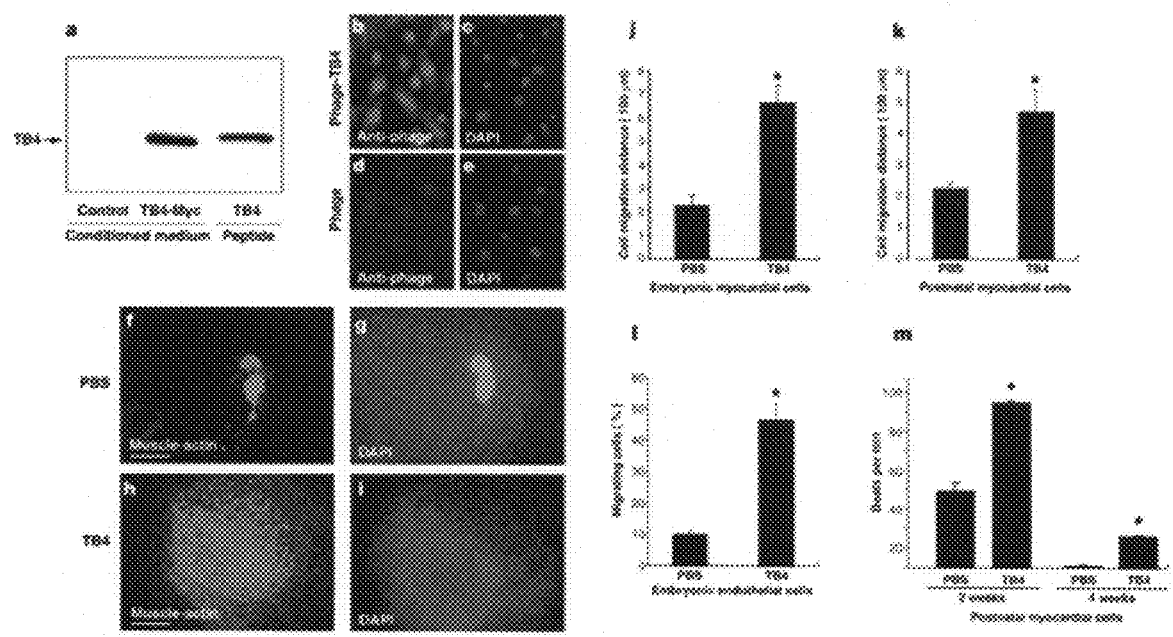
FIGS. 2A-M—Thymosin β4 is secreted and promotes cardiac cell migration and survival.

To test the effects of secreted thymosin β4 on cardiac cell migration, the inventors used an embryonic heart explant system designed to assay cell migration and transformation on a collagen gel (Runyan and Markwald, 1983). Cardiomyocytes from valve-forming regions secrete signals that induce endocardial cell migration onto collagen, but myocardial cells do not normally migrate in significant numbers (FIG. 2F, 2G). In contrast, upon addition of thymosin β4, the inventors observed a large number of spontaneously beating, cardiac muscle actin-positive cells that migrated away from the explant (FIGS. 2H-J, P<0.0001). No significant difference in cell death or proliferative rate based on TdT-mediated dUTP nick end labelling (TUNEL) assay or phospho-histone H3 immunostaining, respectively, was observed in these cells compared to control cells (data not shown).

To test the response of postnatal cardiomyocytes, the inventors cultured primary rat neonatal cardiomyocytes on laminin-coated glass and treated the cells with phosphate-buffered saline (PBS) or thymosin β4. Similar to embryonic cardiomyocytes, the migrational distance of thymosin-β4-treated neonatal cardiomyocytes was significantly increased compared with control (FIG. 2K, P<0.05). In addition to the effects of thymosin β4 on myocardial cell migration, the inventors observed a similar effect on endothelial migration in the embryonic heart explant assay (FIG. 2L, P<0.01).

Primary culture of neonatal cardiomyocytes typically survives for approximately 1 to 2 weeks, with some cells beating for up to 2 weeks when grown on laminin-coated slides in our laboratory. Surprisingly, neonatal cardiomyocytes survived significantly longer upon exposure to thymosin β4, with rhythmically contracting myocytes visible for up to 28 days FIG. 2M. In addition, the rate of beating was consistently faster in thymosin-β4-treated neonatal cardiomyocytes (95 versus 50 beats per minute, P<0.02), indicating either a change in cell-cell communication or cell metabolism (FIG. 2M; see also Supplementary FIGS. 1A-I and 2A-M).

Figure 3:
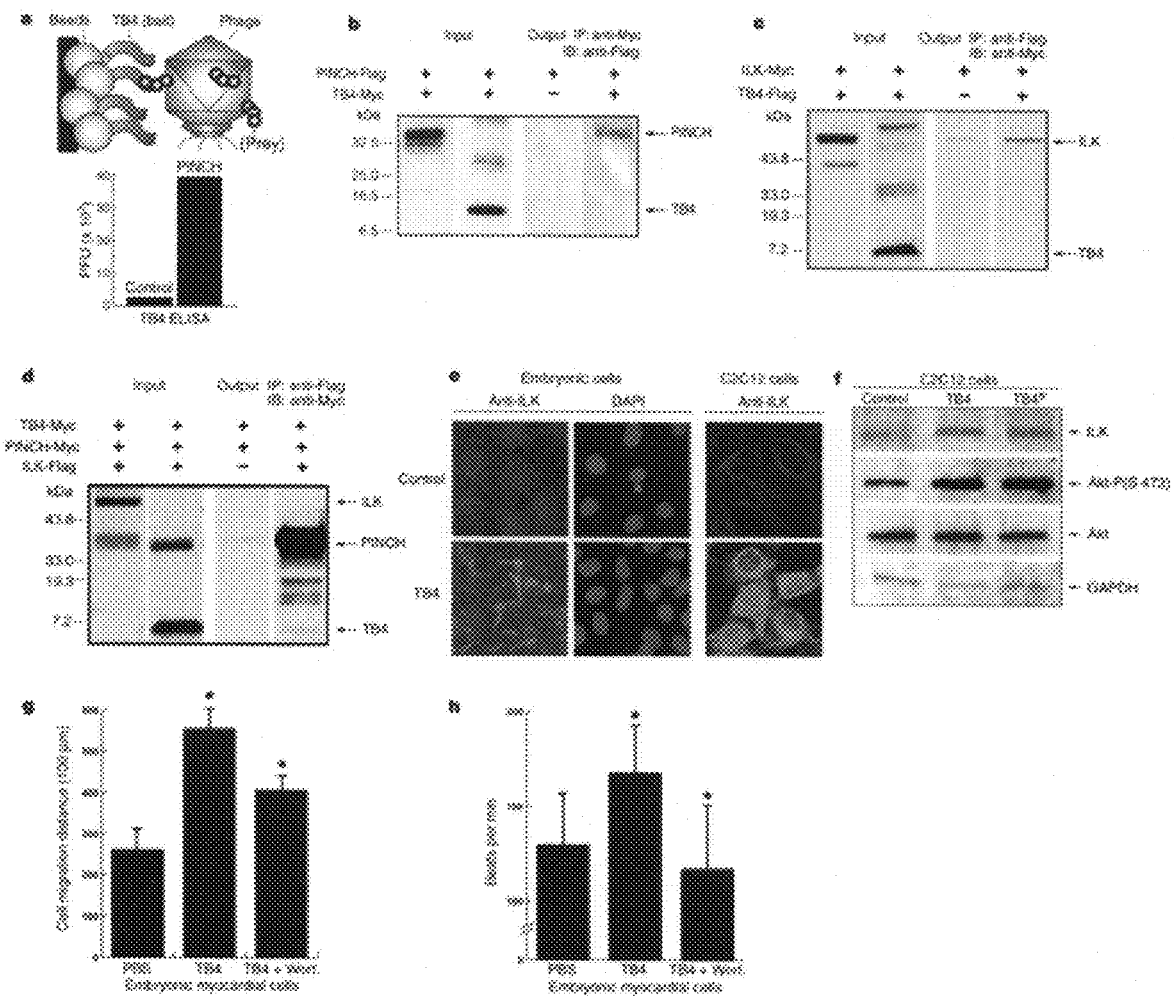
FIGS. 3A-H—Thymosin β4 forms a functional complex with PINCH and ILK resulting in phosphorylation of Akt.

Thymosin β4 activates ILK and Akt. To investigate the potential mechanisms through which thymosin β4 might be influencing cell migration and survival events, the inventors searched for thymosin β4 interacting proteins. The amino terminus of thymosin β4 was fused with affi-gel beads resulting in exposure of the C-terminus, which allowed identification of previously unknown interacting proteins but prohibited association with actin. The inventors synthesized and screened an E9.5-E12.5 mouse heart T7 phage complementary DNA library by phage display, and thymosin-β4-interacting clones were enriched and confirmed by enzyme-linked immunosorbent assay (ELISA, FIG. 3A). PINCH, a LIM domain protein, was most consistently isolated in this screen and interacted with thymosin β4 in the absence of actin (ELISA, FIG. 3A). PINCH and ILK interact directly with one another and indirectly with the actin cytoskeleton as part of a larger complex involved in cell-extracellular matrix interactions known as the focal adhesion complex. PINCH and ILK are required for cell motility (Fukuda et al., 2003; Zhang et al., 2002) and for cell survival, in part by promoting phosphorylation of the serine-threonine kinase Akt, a central kinase in survival and growth signalling pathways (Fukuda et al., 2003; Troussard et al., 2003; Zhang et al., 2002; Brazil et al., 2002). The inventors transfected plasmids encoding thymosin β4 with or without PINCH or ILK in cultured cells and found that thymosin β4 co-precipitated with PINCH or ILK independently (FIGS. 3B, 3C). Moreover, PINCH, ILK and thymosin β4 consistently immunoprecipitated in a common complex, although the interaction of ILK with thymosin β4 was weaker than with PINCH (FIG. 3D). The PINCH interaction with thymosin β4 mapped to the fourth and fifth LIM domains of PINCH, whereas the N-terminal ankryin domain of ILK was sufficient for thymosin β4 interaction (data not shown).

Because recruitment of ILK to the focal adhesion complex is important for its activation, the inventors assayed the effects of thymosin β4 on ILK localization and expression. ILK detection by immunocytochemistry was markedly enhanced around the cell edges after treatment of embryonic heart explants or C2C12 myoblasts with synthetic thymosin β4 protein (10 ng per 100 µl) or thymosin-β4-expressing plasmid (FIG. 3E). Western analysis indicated a modest increase in ILK protein levels in C2C12 cells, suggesting that the enhanced immunofluorescence may be in part due to altered localization by thymosin β4 (FIG. 3F). The inventors found that upon thymosin β4 treatment of C2C12 cells, ILK was functionally activated—evidenced by increased phosphorylation of its known substrate Akt (Troussard et al., 2003) using a phospho-specific antibody to serine 473 of Akt (FIG. 3F)—whereas total Akt protein was unchanged. The similar effects of extracellularly administered thymosin β4 and transfected thymosin β4 were consistent with our previous observations of internalization of the peptide, and suggested an intracellular rather than an extracellular role in signalling for thymosin β4. Because thymosin β4 sequesters the pool of G-actin monomers, the inventors asked whether the effects on ILK activation were dependent on the role of thymosin β4 in regulating the balance between polymerized F-actin and monomeric G-actin. The inventors inhibited F-actin polymerization using C3 transferase and also promoted F-actin formation with an activated Rho (Arai et al., 2002), but neither intervention affected the ILK activation observed after treatment of COS1 or C2C12 cells with thymosin β4 (data not shown).

To determine whether activation of ILK was necessary for the observed effects of thymosin β4, the inventors used a well-described ILK inhibitor, wortmannin, which inhibits ILK's upstream kinase, phosphatidylinositol-3-OH kinase (PI(3)K) (Delcommenne et al., 1998). Using myocardial cell migration and beating frequency as assays for thymosin β4 activity, the inventors cultured embryonic heart explants as described above in the presence of thymosin β4 with or without wortmannin. Although inhibiting PI(3)K affects many pathways, the inventors observed a significant reduction in myocardial cell migration and beating frequency upon inhibition of ILK, consistent with ILK mediation of the effects of thymosin β4 (FIGS. 3G, 3H, P<0.05). Together, these results supported a physiologically significant interaction of thymosin β4-PINCH-ILK within the cell and suggested that this complex may mediate some of the observed effects of thymosin β4 relatively independent of actin polymerization.

Figure 4:
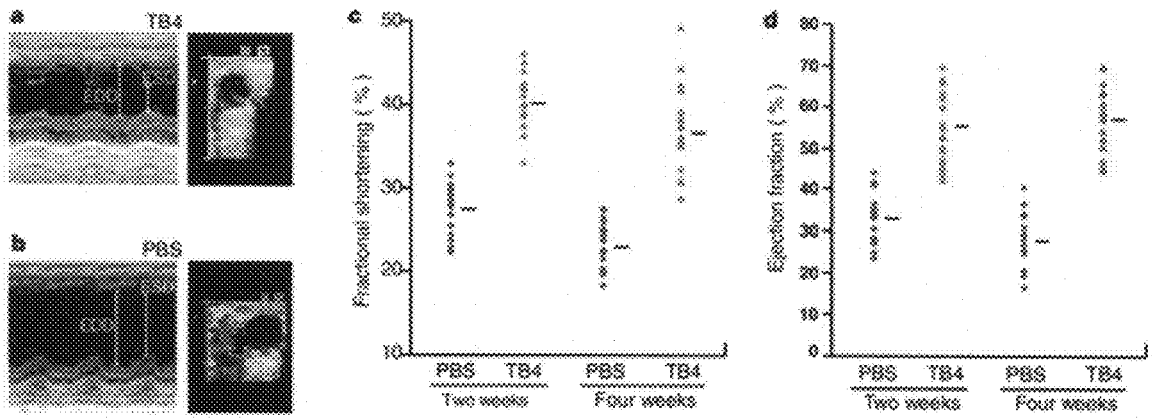
FIGS. 4A-E—Thymosin β4 treatment after coronary ligation improves myocardial function in vivo.

Thymosin β4 promotes cell survival after myocardial infarction and improves cardiac function. Because of the effects of thymosin β4 on cardiac cells in vitro, the inventors tested whether thymosin β4 might aid in cardiac repair in vivo after myocardial damage. The inventors created myocardial infarctions in 58 adult mice by coronary artery ligation and treated half with systemic, intracardiac, or systemic plus intracardiac thymosin β4 immediately after ligation and the other half with PBS (FIGS. 4A-E). All 45 mice that survived 2 weeks later were interrogated for cardiac function by random-blind ultrasonography at 2 and 4 weeks after infarction by multiple measurements of cardiac contraction (FIGS. 4A-D). Four weeks after infarction, left ventricles of control mice had a mean fractional shortening of 23.2±1.2% (n=22, 95% confidence interval); in contrast, mice treated with thymosin β4 had a mean fractional shortening of 37.2±1.8% (n=23, 95% confidence intervals; P<0.0001) (FIGS. 4C, 4E). As a second measure of ventricular function, two-dimensional echocardiographic measurements revealed that the mean fraction of blood ejected from the left ventricle (ejection fraction) in thymosin-β4-treated mice was 57.7±3.2% (n=23, 95% confidence interval; P<0.0001) compared with a mean of 28.2±2.5% (n=22, 95% confidence interval) in control mice after coronary ligation (FIGS. 3D, 3E). The greater than 60% or 100% improvement in cardiac fractional shortening or ejection fraction, respectively, suggested a significant improvement with exposure to thymosin β4, although cardiac function remained depressed compared with sham-operated animals (~60% fractional shortening; ~75% ejection fraction). Finally, the end diastolic dimensions (EDDs) and end systolic dimensions (ESDs) were significantly higher in the control group, indicating that thymosin β4 treatment resulted in decreased cardiac dilation after infarction, consistent with improved function (FIG. 4E). Remarkably, the degree of improvement when thymosin β4 was administered systemically through intraperitoneal injections or only locally within the cardiac infarct was not statistically different, suggesting that the beneficial effects of thymosin β4 probably occurred through a direct effect on cardiac cells rather than through an extracardiac source.

Figure 5:
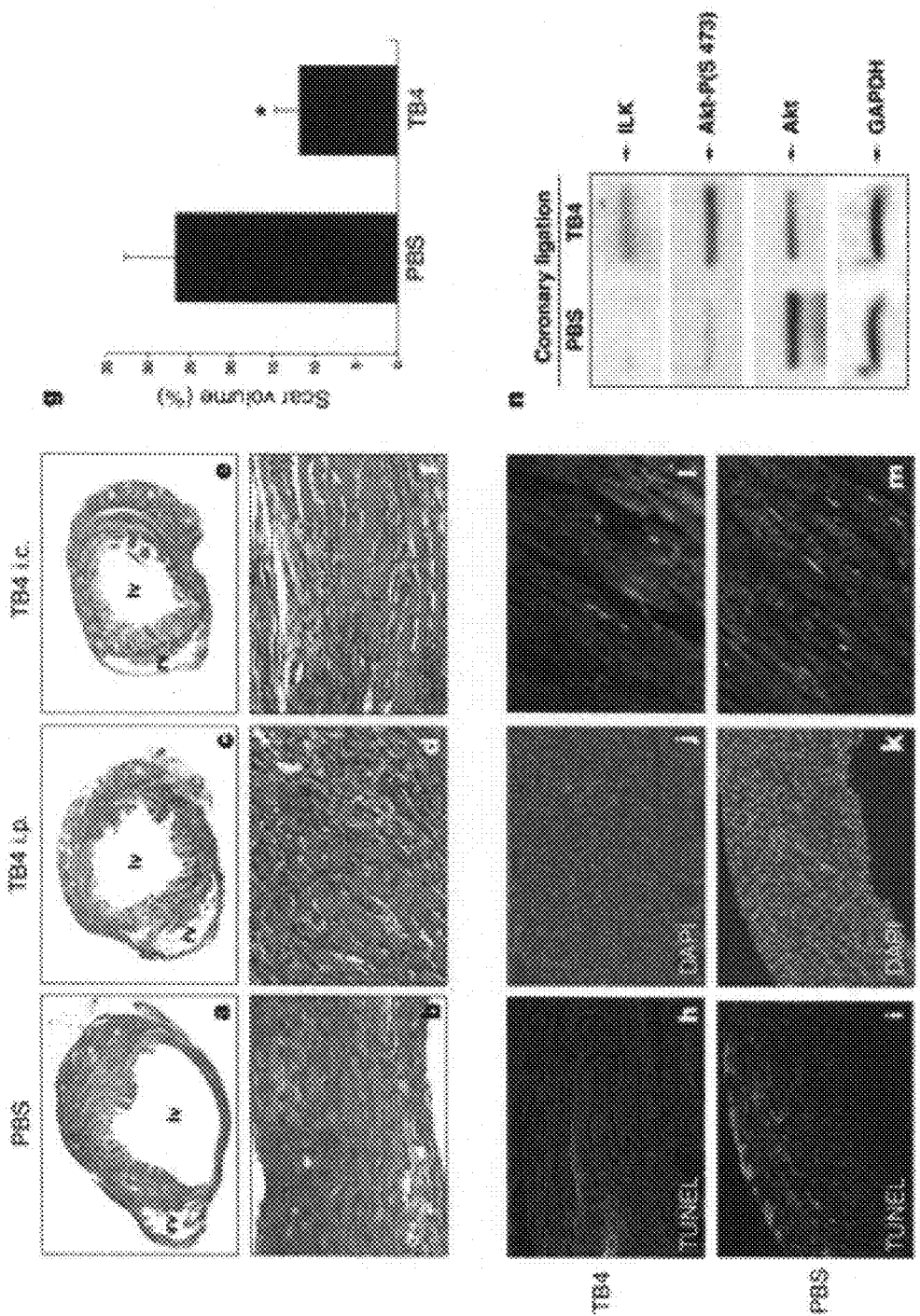

Trichrome stain at three levels of section revealed that the size of scar was reduced in all mice treated with thymosin β4 but was not different between systemic or local delivery of thymosin β4 (FIGS. 5A-F), consistent with the echocardiographic data above. Quantification of scar volume using six levels of sections through the left ventricle of a subset of mice demonstrated significant reduction of scar volume in thymosin-β4-treated mice (FIG. 5G, P<0.05). The inventors did not detect significant cardiomyocyte proliferation or death at 3, 6, 11 or 14 days after coronary ligation in PBS or thymosin-β4-treated hearts (data not shown). However, 24 h after ligation the inventors found a marked decrease in cell death by TUNEL assay (green) in thymosin-β4-treated cardiomyocytes (FIGS. 5H-K), marked by double-labelling with muscle-actin antibody (red) (FIGS. 5L, 5M). TUNEL-positive cells that were also myocytes were rare in the thymosin β4 group but abundant in the control hearts. Consistent with this observation, the inventors found that the left ventricle fractional shortening 3 days after infarction was 39.2±2.34% (n=4, 95% confidence interval) with intracardiac thymosin β4 treatment compared with 28.8±2.26% (n=4, 95% confidence interval) in controls (P<0.02); ejection fraction was 64.2±6.69% or 44.7±8.4%, respectively (P<0.02), suggesting early protection by thymosin β4. Finally, the inventors failed to detect any differences in the number of c-kit, Sca-1 or Abcg2 positive cardiomyocytes between treated and untreated hearts, and the cell volume of cardiomyocytes in thymosin-β4-treated animals was similar to mature myocytes, suggesting that the thymosin-β4-induced improvement was unlikely to be influenced by recruitment of known stem cells into the cardiac lineage (data not shown). Thus, the decreased scar volume and preserved function of thymosin-β4-treated mice were probably due to early preservation of myocardium after infarction through the effects of thymosin β4 on survival of cardiomyocytes.

Similar to cultured cells, the level of ILK protein was increased in heart lysates of mice treated with thymosin β4 after coronary ligation compared with PBS-treated mice (FIG. 5N). Correspondingly, phospho-specific antibodies to Akt-S 473 revealed an elevation in the amount of phosphorylated Akt-S 473 in mice treated with thymosin β4 (FIG. 5N), consistent with the effects of thymosin β4 on ILK described earlier (FIGS. 3E, 3F). These observations in vivo were consistent with the effects of thymosin β4 on cell migration and survival demonstrated in vitro, and suggest that activation of ILK and subsequent stimulation of Akt may in part explain the enhanced cardiomyocyte survival induced by thymosin β4, although it is unlikely that a single mechanism is responsible for the full repertoire of thymosin β4's cellular effects.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

XI. References

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,166,452
U.S. Pat. No. 4,256,108
U.S. Pat. No. 4,265,874
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 4,883,750
U.S. Pat. No. 5,242,974
U.S. Pat. No. 5,279,721
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,436,327
U.S. Pat. No. 5,445,934
U.S. Pat. No. 5,472,672
U.S. Pat. No. 5,527,681
U.S. Pat. No. 5,529,756
U.S. Pat. No. 5,532,128
U.S. Pat. No. 5,545,531
U.S. Pat. No. 5,554,501
U.S. Pat. No. 5,556,752
U.S. Pat. No. 5,561,071
U.S. Pat. No. 5,571,639
U.S. Pat. No. 5,593,839
U.S. Pat. No. 5,599,695
U.S. Pat. No. 5,624,711
U.S. Pat. No. 5,658,734
U.S. Pat. No. 5,700,637
U.S. Pat. No. 5,757,994
U.S. Pat. No. 5,788,166
U.S. Pat. No. 5,838,002
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,986,258
U.S. Pat. No. 6,004,755.
U.S. Pat. RE 35,413
Abbondanzo, *Ann. Diagn. Pathol.*, 3(5):318-327, 1999.
Ahmed, *J. Am. Geriatr. Soc.*, 51(1):123-126, 2003.
Allred et al., *Arch. Surg.*, 125(1):107-113, 1990.
American Heart Association. *Heart Disease and Stroke Statistics*, 2004.
Angel et al., *Mol. Cell. Biol.*, 7:2256, 1987.
Angel et al., *Cell*, 49:729, 1987b.
Angel et al., *Mol. Cell. Biol.*, 7:2256, 1987a.
Anversa and Nadal-Ginard, *Nature* 415, 240-243 (2002).
Arai et al., *J. Biol. Chem.*, 277, 24453-24459 (2002).
Atchison and Perry, *Cell*, 46:253, 1986.
Atchison and Perry, *Cell*, 48:121, 1987.
Bahr et al., *J. Mass Spectrom.*, 32:1111-1116, 1997.
Baichwal and Sugden, *Gene Transfer*, Kucherlapati R, ed., New York, Plenum Press, pp. 117-148, 1986.
Balsam et al., *Nature* 428, 668-673 (2004).
Banerji et al., *Cell*, 27(2 Pt 1):299-308, 1981.
Banerji et al., *Cell*, 33(3):729-740, 1983.
Barnes et al., *J. Biol. Chem.*, 272(17):11510-7, 1997.
Beltrami et al., *Cell* 114, 763-776 (2003).
Bentzley et al., *Anal Chem.*, 68(13):2141-2146, 1996.
Benvenisty and Neshif, *Proc. Nat'l Acad. Sci. USA*, 83:9551-9555, 1986.

Berkhout et al., *Cell*, 59:273-282, 1989.
Bhavsar et al., *Genomics*, 35(1):11-23, 1996.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Brazil et al., *Cell*, 111, 293-303 (2002).
Brown et al. *Immunol. Ser.*, 53:69-82, 1990.
Bucknall et al., *J. Am. Soc. Mass Spectrom.*, 13(9):1015-1027, 2002.
Bucknall et al., *J. Am. Soc. Mass Spectrom.*, 13(9):1015-1027, 2002.
Bulla and Siddiqui, *J. Virol.*, 62:1437, 1986.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Caprioli et al., *Anal. Chem.*, 69:4751, 1997.
Celander and Haseltine, *J. Virology*, 61:269, 1987.
Celander et al., *J. Virology*, 62:1314, 1988.
Chamberlan et al., In: *PCR Protocols*, Innis et al. (Eds.), Academic Press, NY, 272-281, 1990.
Chandler et al., *Cell*, 33:489, 1983.
Chang et al., *Hepatology*, 14:124A (1991).
Chang et al., *Mol. Cell. Biol.*, 9:2153, 1989.
Chatterjee et al., *Proc. Natl. Acad. Sci. USA*, 86:9114, 1989.
Chaurand et al., *Anal Chem.*, 71(23):5263-5270, 1999.
Chen and Okayama, *Mol. Cell Biol.*, 7:2745-2752 (1987).
Chen et al., *Nat. Biotechnol.*, 19:537-542, 2001.
Choi et al., *Cell*, 53:519, 1988.
Coffin, Retroviridae and Their Replication. In: *Virology*, Fields et al., eds., Raven Press, New York, pp. 1437-1500, 1990.
Cohen et al., *J. Cell. Physiol.*, 5:75, 1987.
Conte et al., *J. Heart Lung Transplant.*, 17:679-685, 1998.
Costa et al., *Mol. Cell. Biol.*, 8:81, 1988.
Couch et al., *Am. Rev. Resp. Dis.*, 88:394-403, 1963.
Coupar et al., *Gene*, 68:1-10, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Feo et al., *Ital. Heart J.*, 4:511-513, 2003.
De Jager et al., *Semin. Nucl. Med.*, 23(2):165-179, 1993.
De Villiers et al., *Nature*, 312(5991):242-246, 1984.
Delcommenne et al., *Proc. Natl. Acad. Sci. USA*, 95, 11211-11216 (1998).
Depre et al., *Circ Res.*, 2004.
Deschamps et al., *Science*, 230:1174-1177, 1985.
Desiderio et al., *J. Mass Spectrom.*, 35(6):725-733, 2000.
Desiderio et al., *Methods Mol. Biol.*, 61:57-65, 1996.
DiBianco, R., *Am. J. Med.*, 115:480-488, 2003.
Doolittle and Ben-Zeev, *Methods Mol Biol*, 109:215-237, 1999.
Dubenskyetal., *Proc. Nat'l Acad. Sci. USA*, 81:7529-7533, 1984.
Dumcius et al., *Medicina*, 39:815-822, 2003.
Duncan et al., *Rapid Commun. Mass Spectrom.*, 7:1090, 1993.
Durand et al., *Ann. Med.*, 27:311-317, 1995.
Edbrooke et al., *Mol. Cell. Biol.*, 9:1908, 1989.
Edlund et al., *Science*, 230:912-916, 1985.
European Appln. 0273085
European Appln. 0 364 255
European Appln. 320 308
European Appln. 329 822
Faulstich et al., *Anal. Chem.*, 69(21):4349-4353, 1997.
Fechheimer et al., *Proc Nat'l. Acad. Sci. USA* 84:8463-8467, 1987.
Feng and Holland, *Nature*, 334:6178, 1988.
Fenn et al., *Science*, 246(4926):64-71, 1989.
Ferkol et al., *FASEB J.*, 7:1081-1091, 1993.
Firak and Subramanian, *Mol. Cell. Biol.*, 6:3667, 1986.
Foecking and Hofstetter, *Gene*, 45(1):101-105, 1986.
Fraley et al., *Proc Nat'l. Acad. Sci. USA* 76:3348-3352, 1979
Franz et al., *Cardoscience*, 5(4):235-43, 1994.
Friedmann, *Science*, 244:1275-1281, 1989.
Frohm et al., *Eur. J. Biochem.*, 237, 8692 (1996).
Frohman, In: *PCR Protocols: A Guide To Methods And Applications*, Academic Press, N.Y., 1990.
Fujita et al., *Cell*, 49:357, 1987.
Fukuda et al., *J. Biol. Chem.*, 278, 51324-51333 (2003).
Garg et al., *Nature*, 424, 443-447 (2003).
Garner et al., *Am. J. Physiol. Heart Circ. Physiol.*, 285, 500-509 (2003).
GB Application No. 2 202 328
Ghosh and Bachhawat, In: *Liver Diseases, Targeted Diagnosis and Therapy Using Specific Receptors and Ligands*. Wu et al., eds., Marcel Dekker, New York, pp. 87-104, 1991.
Ghosh-Choudhury et al., *EMBO J*, 6:1733-1739, 1987.
Gilles et al., *Cell*, 33:717, 1983.
Gloss et al., *EMBO J.*, 6:3735, 1987.
Gobom et al., *Anal. Chem.* 72:3320, 2000.
Godbout et al., *Mol. Cell. Biol.*, 8:1169, 1988.
Gomez-Foix et al, *J. Biol. Chem.*, 267:25129-25134, 1992.
Gomez-Marquez et al., *Biochim. Biophys. Acta*, 1306, 187-193 (1996).
Goodboum and Maniatis, *Proc. Natl. Acad. Sci. USA*, 85:1447, 1988.
Goodboum et al., *Cell*, 45:601, 1986.
Goodman and Gilman's The Pharmacological Basis of Therapeutics.
Gopal, *Mol. Cell Biol.*, 5:1188-1190, 1985.
Gopal-Srivastava et al., *J. Mol. Cell. Biol.* 15(12):7081-90, 1995.
Graham and Prevec, In: *Methods in Molecular Biology: Gene Transfer and Expression Protocol*, E. J. Murray, ed., Humana Press, Clifton, N.J., 7:109-128, 1991.
Graham and van der Eb, *Virology*, 52:456-467, 1973.
Graham et al., *J. Gen. Virol.*, 36:59-72, 1977.
Grant et al., *Angiogenesis* 3, 125-135 (1999).
Greene et al., *Immunology Today*, 10:272, 1989
Grosschedl and Baltimore, *Cell*, 41:885, 1985.
Grunhaus and Horwitz, *Seminar in Virology*, 3:237-252, 1992.
Gulbis and Galand, *Hum. Pathol.*, 24(12):1271-1285, 1993.
Hannigan et al., *Nature*, 379:91-96, 1996.
Hardie, G. and Hanks, S. (1995) The Protein Kinase Facts Books, Vol 1:7-20 Academic Press, San Diego, Calif.
Harland and Weintraub, *J. Cell Biol.*, 101:1094-1099, 1985.
Harlow and Lane, Antibodies: A Laboratory manual, Cold Spring Harbor Laboratory, 1988.
Harlow and Lane, In: *Antibodies, a Laboratory Manual*, Cold Spring Harbor Laboratory, 139-281, 1988.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Hermonat and Muzycska, *Proc. Nat'l Acad. Sci. USA*, 81:6466-6470, 1984.
Herr and Clarke, *Cell*, 45:461, 1986.
Hersdorffer et al., *DNA Cell Biol.*, 9:713-723, 1990.
Hertzog et al., *Cell*, 117, 611-623 (2004).

Hirochika et al., *J. Virol.*, 61:2599, 1987.
Hirsch et al., *Mol. Cell. Biol.*, 10:1959, 1990.
Hoffman and Kaplan, *J. Am. Coll. Cardiol.* 39, 1890-1900, 2002.
Holbrook et al., *Virology*, 157:211, 1987.
Horak et al., *Rapid Commun. Mass Spectrom.*, 15(4):241-248, 2001.
Horlick and Benfield, *Mol. Cell. Biol.*, 9:2396, 1989.
Horwich et al., *J. Virol.*, 64:642-650, 1990.
Huang and Wang, *Exp. Hematol.*, 29, 12-18 (2001).
Huang et al., *Cell*, 27:245, 1981.
Huff et al., *Int. J. Biochem. Cell Biol.*, 33, 205-220 (2001).
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc. Natl. Acad. Sci. USA*, 85(24):9436-9440, 1988.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Jespersen et al., *Anal Chem.*, 71(3):660-666, 1999.
Jiang et al., *Biochem. Pharmacol.*, 59:763-772, 2000.
Johnson et al., *Mol. Cell. Biol.*, 9:3393, 1989.
Jones and Shenk, *Cell*, 13:181-188, 1978.
Kabarle et al., *Anal. Chem.* 65(20):972A-986A, 1993.
Kadesch and Berg, *Mol. Cell. Biol.*, 6:2593, 1986.
Kanazawa et al., *Biol. Pharm. Bull.*, 22(4):339-346, 1999.
Kaneda et al., *Science*, 243:375-378, 1989.
Karin et al., *Mol. Cell. Biol.*, 7:606, 1987.
Karin et al., *Mol. Cell. Biol.*, 7:606, 1987.
Katinka et al., *Cell*, 20:393, 1980.
Kato et al., *J. Biol. Chem.*, 266(6):3361-3364, 1991.
Kawamoto et al., *Mol. Cell. Biol.*, 8:267, 1988.
Kazmaier et al., *Anesthesiology*, 89(4):831-817, 1998.
Kelly and Buckingham, *Trends Genet.*, 18, 210-216 (2002).
Kelly et al., *J. Cell Biol.*, 129(2):383-96, 1995.
Kiledjian et al., *Mol. Cell. Biol.*, 8:145, 1988.
Kimura et al., *Dev. Growth Differ.*, 39(3):257-65, 1997.
Klamut et al., *Mol. Cell. Biol.*, 10:193, 1990.
Klein et al., *Nature*, 327:70-73, 1987.
Koch et al., *Mol. Cell. Biol.*, 9:303, 1989.
Kriegler and Botchan, In: *Eukaryotic Viral Vectors*, Gluzman (Ed.), Cold Spring Harbor: Cold Spring Harbor Laboratory, NY, 1982.
Kriegler and Botchan, Mol. Cell. Biol., 3:325, 1983.
Kriegler et al., *Cell*, 38:483, 1984.
Kriegler et al., *Cell*, 53:45, 1988.
Kuhli et al., *Cell*, 50:1057, 1987.
Kunz et al., *Nucl. Acids Res.*, 17:1121, 1989.
Kwoh et al., *Proc. Natl. Acad. Sci. USA*, 86:1173, 1989.
LaPointe et al., *Hypertension* 27(3 Pt 2):715-22, 1996.
LaPointe et al., *J. Biol. Chem.*, 263(19):9075-8, 1988.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Le Gal La Salle et al., *Science*, 259:988-990, 1993.
Lee et al., *Nature*, 294:228, 1981.
Lee et al., *Nucleic Acids Res.*, 12:4191-206, 1984.
Levinson et al., *Nature*, 295:79, 1982.
Levrero et al., *Gene*, 101: 195-202, 1991.
Li et al., *J. Cell Sci.*, 112:4589-4599, 1999.
Li et al., *Trends Biotechnol.*, 18:151, 2000.
Lin and and Morrison-Bogorad, *J. Mol. Neurosci.*, 2, 35-44 (1990).
Lin et al., *Mol. Cell. Biol.*, 10:850, 1990.
Lovelace et al., *J. Chromatogr.*, 562(1-2):573-584, 1991.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Lynn et al., *J. Mol. Evol.*, 48(5):605-614, 1999.
Macejak and Sarnow, *Nature*, 353:90-94, 1991.
Majors and Varmus, *Proc. Natl. Acad. Sci. USA*, 80:5866, 1983.
Malinda et al., *J. Invest. Dermatol.* 113, 364-368 (1999).
Mangi et al., *Nature Med.*, 9, 1195-1201 (2003).
Mann et al., *Cell*, 33:153-159, 1983.
Manoria and Manoria, *J. Indian. Med. Assoc.*, 101(5):311-312, 2003.
Marie et al., *Anal. Chem.*, 72(20):5106-5114, 2000.
Marinissen et al., *Mol. Cell*, 14, 29-41 (2004).
Markowitz et al., *J. Virol.*, 62:1120-1124, 1988.
McNeall et al., *Gene*, 76:81, 1989.
Miketova et al., *Mol. Biotechnol.*, 8(3):249-253, 1997.
Miksicek et al., *Cell*, 46:203, 1986.
Mirgorodskaya et al., *Rapid Commun. Mass Spectrom.*, 14(14):1226-1232, 2000.
Mora et al., *Int. J. Immunopharmacol.*, 19, 1-8 (1997).
Mordacq and Linzer, *Genes and Dev.*, 3:760, 1989.
Moreau et al., *Nucl. Acids Res.*, 9:6047, 1981.
Moss et al., *J. Gen. Physiol.*, 108(6):473-84, 1996.
Muddiman et al., *Fres. J Anal. Chem.*, 354:103, 1996.
Mueller and Wold, *Science*, 246:780-786, 1989.
Muesing et al., *Cell*, 48:691, 1987.
Murry et al., *Nature* 428, 664-668 (2004).
Nakamura et al., In: *Handbook of Experimental Immunology* (4th Ed.), Weir et al. (Eds), 1:27, Blackwell Scientific Publ., Oxford, 1987.
Nelson et al., *Anal. Chem.*, 66:1408, 1994.
Ng et al., *Nuc. Acids Res.*, 17:601, 1989.
Nguyen et al., *J. Chromatogr. A.*, 705(1):21-45, 1995.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nikolopoulos and Turner, *J. Cell Biol.*, 151:1435-1448, 2000.
Ohara et al., *Proc. Natl. Acad. Sci. USA*, 86:5673-5677, 1989.
Olave et al., *Annu. Rev. Biochem.*, 71, 755-781 (2002).
Olski et al., *J. Cell Sci.*, 114:525-538, 2001.
Ondek et al., *EMBO J.*, 6:1017, 1987.
Orlic et al. *Nature* 410, 701-705 (2001).
Ornitz et al., *Mol. Cell. Biol.*, 7:3466, 1987.
Palmiter et al., *Nature*, 300:611, 1982.
Paskind et al., *Virology*, 67:242-248, 1975.
PCT Appln, WO 84/03564
PCT Appln. PCT/US87/00880
PCT Appln. PCT/US89/01025
PCT Appln. WO 88/10315,
PCT Appln. WO 89/06700
PCT Appln. WO 90/07641
Pech et al., *Mol. Cell. Biol.*, 9:396, 1989.
Pelletier and Sonenberg, *Nature*, 334:320-325, 1988.
Perales et al., *Proc. Nat'l Acad. Sci. USA*, 91(9):4086-4090, 1994.
Perez-Stable and Constantini, *Mol. Cell. Biol.*, 10:1116, 1990.
Philp et al., *Wound Rep. Reg.*, 11, 19-24 (2003).
Physicians Desk Reference.
Picard and Schafffner, *Nature*, 307:83, 1984.

Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Potter et al., *Proc. Nat'l Acad. Sci. USA*, 81:7161-7165, 1984.
Queen and Baltimore, *Cell*, 35:741, 1983.
Quinn et al., *Mol. Cell. Biol.*, 9:4713, 1989.
Racher et al., *Biotechnology Techniques*, 9:169-174, 1995.
Ragot et al.," *Nature*, 361:647-650, 1993.
Redondo et al., *Science*, 247:1225, 1990.
Reinhold-Hurek and Shub, *Nature*, 357:173-176, 1992.
Reisman and Rotter, *Mol. Cell. Biol.*, 9:3571, 1989.
Remington's Pharmaceutical Sciences and The Merck Index, 11th Edition.
Renan, *Radiother. Oncol.*, 19:197-218, 1990.
Resendez Jr. et al., *Mol. Cell. Biol.*, 8:4579, 1988.
Rich et al., *Hum. Gene Ther.*, 4:461-476, 1993.
Ridgeway, Mammalian Expression Vectors, In: *Vectors: A Survey of Molecular Cloning Vectors and Their Uses*, Rodriguez et al., eds., Stoneham: Butterworth, pp. 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Roepstorff, *EXS.* 2000; 88:81-97, 2000.
Rosen et al., *Cell*, 41:813, 1988.
Rosenfeld et al., *Science*, 252:431-434, 1991.
Rosenfeld, et al., *Cell*, 68:143-155, 1992.
Roux et al., *Proc. Nat'l Acad. Sci. USA*, 86:9079-9083, 1989.
Runyan and Markwald, *Dev. Biol.*, 95, 108-114 (1983).
Safer et al., *J. Biol. Chem.*, 266, 4029-4032 (1991).
Sakai et al., *Genes and Dev.*, 2:1144, 1988.
Sambrook et al., *Molecular Cloning: A Laboratory Manual*, 2nd Ed., Cold Spring Harbor Press, Cold Spring Harbor, N.Y., 1989.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Sosne et al., *Exp. Eye Res.* 74, 293-299 (2002).
Spalholz et al., *Cell*, 42:183, 1985.
Spandau and Lee, *J. Virology*, 62:427, 1988.
Spandidos and Wilkie, *EMBO J.*, 2:1193, 1983.
Srivastava and Olson, *Nature* 407, 221-226 (2000).
Stephens and Hentschel, *Biochem. J.*, 248:1, 1987.
Stoeckli et al., *Nat. Med.*, 7(4):493-496, 2001.
Stratford-Perricaudet and Perricaudet, In: *Human Gene Transfer*, O. Cohen-Haguenauer et al., eds., John Libbey Eurotext, France, pp. 51-61, 1991.
Stratford-Perricaudet et al., *Hum. Gene. Ther.*, 1:241-256, 1990.
Stuart et al., *Nature*, 317:828, 1985.
Sullivan and Peterlin, *Mol. Cell. Biol.*, 7:3315, 1987.
Sun et al., *J. Biol. Chem.*, 271, 9223-9230 (1996).
Swartzendruber and Lehman, *J. Cell. Physiology*, 85:179, 1975.
Takach et al., *J. Protein Chem.*, 16:363, 1997.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Temin, In: *Gene Transfer*, Kucherlapati R, ed., New York, Plenum Press, pp. 149-188, 1986.
The Merck Index, O'Neil et al., ed., 13$^{th}$ Ed., 2001.
Thiesen et al., *J. Virology*, 62:614, 1988.
Top et al., *J. Infect. Dis.*, 124:155-160, 1971.
Treisman, *Cell*, 42:889, 1985.
Tronche et al., *Mol. Biol. Med.*, 7:173, 1990.
Troussard et al, *J. Biol. Chem.*, 278, 22374-22378 (2003).
Trudel and Constantini, *Genes and Dev.*, 6:954, 1987.
Tu et al., *J. Cell Biol.*, 153:585-598, 2001.
Tu et al., *Mol. Cell. Biol.*, 19:2425-2434, 1999.
Tur-Kaspa et al., *Mol. Cell Biol.*, 6:716-718, 1986.
Tyndell et al., *Nuc. Acids. Res.*, 9:6231, 1981.
Van den Hoff et al., *Dev. Biol.*, 212, 477-490 (1999).
Vannice and Levinson, *J. Virology*, 62:1305, 1988.
Varmus et al., *Cell*, 25:23-36, 1981.
Vasseur et al., *Proc Natl. Acad. Sci. USA*, 77:1068, 1980.
Velyvis et al., *J. Biol. Chem.*, 276:4932-4939, 2001.
Villanueva et al., *Enzyme Microb. Technol.*, 29:99, 1999.
Wagner et al., *Proc. Nat'l Acad. Sci. USA* 87(9):3410-3414, 1990.
Walker et al., *Nucleic Acids Res.*, 20(7):1691-1696, 1992.
Wang and Calame, *Cell*, 47:241, 1986.
Wang et al., *Anal. Chem.*, 72(21):5285-5289, 2000.
Wang et al., *J. Biol. Chem.*, 274(50):35343-35350, 1999.
Weber et al., *Cell*, 36:983, 1984.
Weinberger et al. *Mol. Cell. Biol.*, 8:988, 1984.
Winoto and Baltimore, *Cell*, 59:649, 1989.
Wittmann et al., *Biotechnol. Bioeng.*, 72:642, 2001.
Wong et al., *Gene*, 10:87-94, 1980.
Wu and Wu, *Adv. Drug Delivery Rev.*, 12:159-167, 1993.
Wu and Wu, *Biochemistry*, 27:887-892, 1988.
Wu and Wu, *J. Biol. Chem.*, 262:4429-4432, 1987.
Wu et al., *J. Biol. Chem.*, 273:528-536, 1998.
Wu et al., *Mol. Cell Biochem.*, 203(1-2):59-71, 2000.
Wu, *J. Cell Sci.*, 112:4485-4489, 1999.
Yamagishi et al., *Genes Dev.*, 17, 269-281 (2003).
Yamaji et al., *J. Cell Biol.*, 153:1251-1264, 2001.
Yamauchi-Takihara, et al., *Proc. Nat'l Acad. Sci. USA*, 86(10):3504-8, 1989.
Yang et al., *J. Biol. Chem.*, 275:26892-36898, 2000.
Yang et al., *Proc Natl. Acad. Sci. USA*, 87:9568-9572, 1990.
Yu et al., *J. Biol. Chem.*, 268, 502-509 (1993).
Yutzey et al. *Mol. Cell. Biol.*, 9:1397, 1989.
Zelenin et al., *FEBS Lett.*, 280:94-96, 1991.
Zhang et al., *J. Cell Sci.*, 115, 4777-4786 (2002).
Zhong et al., *Clin. Chem. ACTA.*, 313:147, 2001.
Ziober and Kramer, *J. Bio. Chem.*, 271(37):22915-22, 1996.
Zweigenbaum et al., *Anal. Chem.*, 71(13):2294-300, 1999.
Zweigenbaum et al., *J. Pharm. Biomed. Anal.*, 23(4):723-733, 2000.

What is claimed is:

1. A method of screening for an inhibitor of damage associated with myocardial ischemia comprising:
   (a) providing a myocyte expressing integrin-linked kinase (ILK) and/or Akt/protein kinase B (PKB);
   (b) treating said myocyte with a candidate protein, protein fragment, or a small molecule; and
   (c) measuring expression, activity or stability of ILK and/or Akt/PKB, in said myocyte,
   wherein an increase in the expression, activity or stability of ILK and/or Akt/PKB in said myocyte, as compared to a cell not treated with said candidate substance, identifies said candidate substance as an inhibitor of damage associated with myocardial ischemia.

2. The method of claim 1, wherein said myocyte is an isolated myocyte.

3. The method of claim 2, wherein said isolated myocyte is a cardiomyocyte.

4. The method of claim 1, wherein said myocyte is comprised in isolated intact tissue.

5. The method of claim 1, wherein said myocyte is a neonatal rat ventricular myocyte.

6. The method of claim 3, wherein said cardiomyocyte is located in vivo in a functioning intact heart muscle.

7. The method of claim 6, wherein said functioning intact heart muscle is subjected to an ischemic event.

8. The method of claim 1, wherein expression is measured using a reporter protein coding region operably linked to an ILK or Akt/PKB promoter.

9. The method of claim 8, wherein said reporter protein is luciferase, β-gal, or green fluorescent protein.

10. The method of claim 1, wherein expression is measured using hybridization of a nucleic acid probe to a target mRNA or amplified nucleic acid product.

11. The method of claim 1, wherein expression is measured by assessing protein levels.

12. The method of claim 11, wherein assessing proteins levels comprises immunologic detection or mass spectrometry.

13. The method of claim 1, further comprising measuring cell toxicity.

14. The method of claim 1, wherein activity is measured by assessing incorporation of labeled phosphate into a target.

15. The method of claim 1, wherein stability is measured by ILK/Akt complex formation.

16. The method of claim 1, wherein stability is measured by ILK and/or Akt protein turnover.

* * * * *